United States Patent
Hayashi et al.

(10) Patent No.: US 10,550,153 B2
(45) Date of Patent: Feb. 4, 2020

(54) PEPTIDE OR PHARMACEUTICALLY ACCEPTABLE SALT THEREOF, OR PRODRUG THEREOF

(71) Applicants: Tokyo University of Pharmacy & Life Sciences, Hachioji-shi, Tokyo (JP); National Cerebral and Cardiovascular Center, Suita, Osaka (JP); Kyoto Pharmaceutical University, Kyoto-shi, Kyoto (JP)

(72) Inventors: Yoshio Hayashi, Hachioji (JP); Kentaro Takayama, Hachioji (JP); Mikiya Miyazato, Suita (JP); Kenji Kangawa, Suita (JP); Kenji Mori, Suita (JP); Akira Yamamoto, Kyoto (JP); Toshiyasu Sakane, Kyoto (JP)

(73) Assignees: TOKYO UNIVERSITY OF PHARMACY & LIFE SCIENCES, Tokyo (JP); NATIONAL CEREBRAL AND CARDIOVASCULAR CENTER, Osaka (JP); KYOTO PHARMACEUTICAL UNIVERSITY, Kyoto (JP)

( * ) Notice: Subject to any disclaimer, the term of this patent is extended or adjusted under 35 U.S.C. 154(b) by 0 days.

(21) Appl. No.: 16/478,966

(22) PCT Filed: Jan. 19, 2018

(86) PCT No.: PCT/JP2018/001651
§ 371 (c)(1),
(2) Date: Jul. 18, 2019

(87) PCT Pub. No.: WO2018/135641
PCT Pub. Date: Jul. 26, 2018

(65) Prior Publication Data
US 2019/0359652 A1    Nov. 28, 2019

(30) Foreign Application Priority Data
Jan. 20, 2017 (JP) .................. 2017-008301

(51) Int. Cl.
A61K 38/03 (2006.01)
C07K 7/06 (2006.01)
A61P 3/04 (2006.01)
A61K 38/00 (2006.01)

(52) U.S. Cl.
CPC ...... *C07K 7/06* (2013.01); *A61P 3/04* (2018.01); *A61K 38/00* (2013.01)

(58) Field of Classification Search
None
See application file for complete search history.

(56) References Cited

U.S. PATENT DOCUMENTS

| 2007/0244048 A1 | 10/2007 | Marsh et al. |
| 2012/0094899 A1 | 4/2012 | Asami et al. |
| 2017/0037103 A1 | 2/2017 | Ruchala et al. |

FOREIGN PATENT DOCUMENTS

| WO | 2007109135 A2 | 9/2007 |
| WO | 2010116752 A1 | 10/2010 |
| WO | 2015095719 A1 | 6/2015 |

OTHER PUBLICATIONS

Takayama, J. Med. Chem. 2014, 57, 6583-6593 (Year: 2014).*
Blondelle, Antimicrobial Agents and Chemotherapy, Jan. 1999, p. 106-114 (Year: 1999).*
Takayama, et al; Peptide Science; vol. 106; No. 4; 2016; pp. 440-445 (Year: 2016).*
E. D. Micewicz, et al; Small lipidated anti-obesity compounds derived from neuromedin U; European Journal of Medicinal Chemistry; vol. 101; 2015; pp. 616-626.
P. Ingallinella, et al; PEGylation of neuromedin U yields a promising candidate for the treatment of obesity and diabetes; Bioorganic & Medicinal Chemistry; vol. 20; 2012; pp. 4751-4759.
K. Takayama, et al; Discovery of selective hexapeptide agonists to human neuromedin U receptors types 1 and 2; Journal of Medicinal Chemistry; vol. 57; No. 15; 2014; pp. 6583-6593.
K. Takayama, et al; Medicinal Chemistry of Mid-sized Molecules on Biologically Active Peptides; Journal of the Society Synthetic Organic Chemistry; vol. 73; No. 7; 2015; pp. 737-748.
K. Takayama, et al; Discovery of Human Neuromedin U Receptor Type 2-Selective Hexapeptide Agonists; Peptide Science; vol. 2014; 2015; pp. 59-60.
K. Takayama, et al; Discovery of potent hexapeptide agonists to human neuromedin u receptor 1 and identification of their serum metabolites; ACS Med. Chem. Lett.; vol. 6; No. 3; 2015; pp. 302-307.
K. Takayama, et al; Identification of a degrading enzyme in human serum that hydrolyzes a C-terminal core sequence of neuromedin U; Peptide Science; vol. 106; No. 4; 2016; pp. 440-445.
International Search Report dated Apr. 24, 2018 for PCT/JP2018/001651 and English translation.

* cited by examiner

*Primary Examiner* — Satyanarayana R Gudibande
(74) *Attorney, Agent, or Firm* — Lucas & Mercanti, LLP

(57) ABSTRACT

To provide a peptide that selectively activates type 2 neuromedin U receptor and is chemically stable under physiological conditions. A peptide represented by Formula (1) described in the specification.

11 Claims, 10 Drawing Sheets
Specification includes a Sequence Listing.

```
                        SEQUENCE LISTING

<160> NUMBER OF SEQ ID NOS: 72

<210> SEQ ID NO 1
    <211> LENGTH: 6
    <212> TYPE: PRT
    <213> ORGANISM: Artificial Sequence
    <220> FEATURE:
    <223> OTHER INFORMATION: NMUR2 Selective Agonist
    <220> FEATURE:
    <221> NAME/KEY: BINDING
    <222> LOCATION: (3)..(3)
    <223> OTHER INFORMATION: Dbu

<400> SEQUENCE: 1

Leu Leu Xaa Pro Arg Asn
    1               5

<210> SEQ ID NO 2
    <211> LENGTH: 6
    <212> TYPE: PRT
    <213> ORGANISM: Artificial Sequence
    <220> FEATURE:
    <223> OTHER INFORMATION: NMUR2 Selective Agonist
    <220> FEATURE:
    <221> NAME/KEY: BINDING
    <222> LOCATION: (3)..(3)
    <223> OTHER INFORMATION: Orn

<400> SEQUENCE: 2

Leu Leu Xaa Pro Arg Asn
    1               5

<210> SEQ ID NO 3
    <211> LENGTH: 6
    <212> TYPE: PRT
    <213> ORGANISM: Artificial Sequence
    <220> FEATURE:
    <223> OTHER INFORMATION: NMUR2 Selective Agonist
    <220> FEATURE:
    <221> NAME/KEY: BINDING
    <222> LOCATION: (3)..(3)
```

-continued

```
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 3

Leu Leu Xaa Xaa Arg Asn
1               5

<210> SEQ ID NO 4
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu

<400> SEQUENCE: 4

Val Leu Xaa Pro Arg Asn
1               5

<210> SEQ ID NO 5
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nva
<220> FEATURE:
<221> NAME/KEY: BINDING
<222> LOCATION: (3)..(3)
<223> OTHER INFORMATION: Dbu

<400> SEQUENCE: 5

Xaa Leu Xaa Pro Arg Asn
1               5

<210> SEQ ID NO 6
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu

<400> SEQUENCE: 6

Ile Leu Xaa Pro Arg Asn
1               5

<210> SEQ ID NO 7
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nle
<220> FEATURE:
<221> NAME/KEY: BINDING
```

```
<222> LOCATION: (3)..(3)
<223> OTHER INFORMATION: Dbu

<400> SEQUENCE: 7

Xaa Leu Xaa Pro Arg Asn
1               5

<210> SEQ ID NO 8
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 2-Cyclohexyl glycine
<220> FEATURE:
<221> NAME/KEY: BINDING
<222> LOCATION: (3)..(3)
<223> OTHER INFORMATION: Dbu

<400> SEQUENCE: 8

Xaa Leu Xaa Pro Arg Asn
1               5

<210> SEQ ID NO 9
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (3)..(3)
<223> OTHER INFORMATION: Dbu

<400> SEQUENCE: 9

Xaa Leu Xaa Pro Arg Asn
1               5

<210> SEQ ID NO 10
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu

<400> SEQUENCE: 10

Thr Leu Xaa Pro Arg Asn
1               5

<210> SEQ ID NO 11
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Dbu
<220> FEATURE:
```

```
<221> NAME/KEY: BINDING
<222> LOCATION: (3)..(3)
<223> OTHER INFORMATION: Dbu

<400> SEQUENCE: 11

Xaa Leu Xaa Pro Arg Asn
1               5

<210> SEQ ID NO 12
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu

<400> SEQUENCE: 12

Asn Leu Xaa Pro Arg Asn
1               5

<210> SEQ ID NO 13
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu

<400> SEQUENCE: 13

Leu Val Xaa Pro Arg Asn
1               5

<210> SEQ ID NO 14
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nva
<220> FEATURE:
<221> NAME/KEY: BINDING
<222> LOCATION: (3)..(3)
<223> OTHER INFORMATION: Dbu

<400> SEQUENCE: 14

Leu Xaa Xaa Pro Arg Asn
1               5

<210> SEQ ID NO 15
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu

<400> SEQUENCE: 15

Leu Ile Xaa Pro Arg Asn
```

```
1               5

<210> SEQ ID NO 16
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nle
<220> FEATURE:
<221> NAME/KEY: BINDING
<222> LOCATION: (3)..(3)
<223> OTHER INFORMATION: Dbu

<400> SEQUENCE: 16

Leu Xaa Xaa Pro Arg Asn
1               5

<210> SEQ ID NO 17
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: 2-Cyclohexyl glycine
<220> FEATURE:
<221> NAME/KEY: BINDING
<222> LOCATION: (3)..(3)
<223> OTHER INFORMATION: Dbu

<400> SEQUENCE: 17

Leu Xaa Xaa Pro Arg Asn
1               5

<210> SEQ ID NO 18
<211> LENGTH: 7
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (4)..(4)
<223> OTHER INFORMATION: Dbu

<400> SEQUENCE: 18

Xaa Leu Leu Xaa Pro Arg Asn
1               5

<210> SEQ ID NO 19
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: 2-Pyridylalanine

<400> SEQUENCE: 19
```

Leu Leu Xaa Pro Arg Asn
1               5

<210> SEQ ID NO 20
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: 3-Pyridylalanine

<400> SEQUENCE: 20

Leu Leu Xaa Pro Arg Asn
1               5

<210> SEQ ID NO 21
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: 4-Pyridylalanine

<400> SEQUENCE: 21

Leu Leu Xaa Pro Arg Asn
1               5

<210> SEQ ID NO 22
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn

<400> SEQUENCE: 22

Val Leu Xaa Pro Arg Asn
1               5

<210> SEQ ID NO 23
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nva
<220> FEATURE:
<221> NAME/KEY: BINDING
<222> LOCATION: (3)..(3)
<223> OTHER INFORMATION: Orn

<400> SEQUENCE: 23

Xaa Leu Xaa Pro Arg Asn
1               5

<210> SEQ ID NO 24
<211> LENGTH: 6
<212> TYPE: PRT

```
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn

<400> SEQUENCE: 24

Ile Leu Xaa Pro Arg Asn
1               5

<210> SEQ ID NO 25
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nle
<220> FEATURE:
<221> NAME/KEY: BINDING
<222> LOCATION: (3)..(3)
<223> OTHER INFORMATION: Orn

<400> SEQUENCE: 25

Xaa Leu Xaa Pro Arg Asn
1               5

<210> SEQ ID NO 26
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 2-Cyclohexyl glycine
<220> FEATURE:
<221> NAME/KEY: BINDING
<222> LOCATION: (3)..(3)
<223> OTHER INFORMATION: Orn

<400> SEQUENCE: 26

Xaa Leu Xaa Pro Arg Asn
1               5

<210> SEQ ID NO 27
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (3)..(3)
<223> OTHER INFORMATION: Orn

<400> SEQUENCE: 27

Xaa Leu Xaa Pro Arg Asn
1               5

<210> SEQ ID NO 28
<211> LENGTH: 6
```

```
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn

<400> SEQUENCE: 28

Thr Leu Xaa Pro Arg Asn
1               5

<210> SEQ ID NO 29
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn

<400> SEQUENCE: 29

Asn Leu Xaa Pro Arg Asn
1               5

<210> SEQ ID NO 30
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nva
<220> FEATURE:
<221> NAME/KEY: BINDING
<222> LOCATION: (3)..(3)
<223> OTHER INFORMATION: Orn

<400> SEQUENCE: 30

Leu Xaa Xaa Pro Arg Asn
1               5

<210> SEQ ID NO 31
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn

<400> SEQUENCE: 31

Leu Ile Xaa Pro Arg Asn
1               5

<210> SEQ ID NO 32
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
```

```
<223> OTHER INFORMATION: Nle
<220> FEATURE:
<221> NAME/KEY: BINDING
<222> LOCATION: (3)..(3)
<223> OTHER INFORMATION: Orn

<400> SEQUENCE: 32

Leu Xaa Xaa Pro Arg Asn
1               5

<210> SEQ ID NO 33
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: 2-Cyclohexyl glycine
<220> FEATURE:
<221> NAME/KEY: BINDING
<222> LOCATION: (3)..(3)
<223> OTHER INFORMATION: Orn

<400> SEQUENCE: 33

Leu Xaa Xaa Pro Arg Asn
1               5

<210> SEQ ID NO 34
<211> LENGTH: 7
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (4)..(4)
<223> OTHER INFORMATION: Orn

<400> SEQUENCE: 34

Xaa Leu Leu Xaa Pro Arg Asn
1               5

<210> SEQ ID NO 35
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 35

Leu Leu Xaa Xaa Arg Asn
1               5

<210> SEQ ID NO 36
<211> LENGTH: 6
<212> TYPE: PRT
<213> ORGANISM: Artificial Sequence
```

```
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 36

Val Leu Xaa Xaa Arg Asn
1               5

<210> SEQ ID NO 37
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nva
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 37

Xaa Leu Xaa Xaa Arg Asn
1               5

<210> SEQ ID NO 38
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 38

Ile Leu Xaa Xaa Arg Asn
1               5

<210> SEQ ID NO 39
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nle
<220> FEATURE:
<221> NAME/KEY: BINDING
<222> LOCATION: (3)..(3)
<223> OTHER INFORMATION: Dbu
<220> FEATURE:
<221> NAME/KEY: BINDING
```

```
<222> LOCATION: (4)..(4)
<223> OTHER INFORMATION: Homoproline

<400> SEQUENCE: 39

Xaa Leu Xaa Xaa Arg Asn
1               5

<210> SEQ ID NO 40
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 2-Cyclohexyl glycine
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 40

Xaa Leu Xaa Xaa Arg Asn
1               5

<210> SEQ ID NO 41
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 41

Xaa Leu Xaa Xaa Arg Asn
1               5

<210> SEQ ID NO 42
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 42

Thr Leu Xaa Xaa Arg Asn
1               5
```

```
<210> SEQ ID NO 43
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Dbu
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 43

Xaa Leu Xaa Xaa Arg Asn
1               5

<210> SEQ ID NO 44
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 44

Asn Leu Xaa Xaa Arg Asn
1               5

<210> SEQ ID NO 45
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 45

Leu Val Xaa Xaa Arg Asn
1               5

<210> SEQ ID NO 46
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nva
<220> FEATURE:
```

```
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 46

Leu Xaa Xaa Xaa Arg Asn
1               5

<210> SEQ ID NO 47
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 47

Leu Ile Xaa Xaa Arg Asn
1               5

<210> SEQ ID NO 48
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nle
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline

<400> SEQUENCE: 48

Leu Xaa Xaa Xaa Arg Asn
1               5

<210> SEQ ID NO 49
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: 2-Cyclohexyl glycine
<220> FEATURE:
<221> NAME/KEY: BINDING
<222> LOCATION: (3)..(3)
<223> OTHER INFORMATION: Dbu
<220> FEATURE:
<221> NAME/KEY: BINDING
<222> LOCATION: (4)..(4)
<223> OTHER INFORMATION: Homoproline
```

```
<400> SEQUENCE: 49

Leu Xaa Xaa Xaa Arg Asn
1               5

<210> SEQ ID NO 50
<211> LENGTH: 7
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (4)..(4)
<223> OTHER INFORMATION: Dbu
<220> FEATURE:
<221> NAME/KEY: BINDING
<222> LOCATION: (5)..(5)
<223> OTHER INFORMATION: Homoproline

<400> SEQUENCE: 50

Xaa Leu Leu Xaa Xaa Arg Asn
1               5

<210> SEQ ID NO 51
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: 2-Pyridylalanine
<220> FEATURE:
<221> NAME/KEY: BINDING
<222> LOCATION: (4)..(4)
<223> OTHER INFORMATION: Homoproline

<400> SEQUENCE: 51

Leu Leu Xaa Xaa Arg Asn
1               5

<210> SEQ ID NO 52
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: 3-Pyridylalanine
<220> FEATURE:
<221> NAME/KEY: BINDING
<222> LOCATION: (4)..(4)
<223> OTHER INFORMATION: Homoproline

<400> SEQUENCE: 52

Leu Leu Xaa Xaa Arg Asn
1               5

<210> SEQ ID NO 53
<211> LENGTH: 6
<212> TYPE: PRT
<213> ORGANISM: Artificial Sequence
<220> FEATURE:
<223> OTHER INFORMATION: NMUR2 Selective Agonist
```

```
<220> FEATURE:
<221> NAME/KEY: BINDING
<222> LOCATION: (3)..(3)
<223> OTHER INFORMATION: 4-Pyridylalanine
<220> FEATURE:
<221> NAME/KEY: BINDING
<222> LOCATION: (4)..(4)
<223> OTHER INFORMATION: Homoproline

<400> SEQUENCE: 53

Leu Leu Xaa Xaa Arg Asn
1               5

<210> SEQ ID NO 54
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 54

Val Leu Xaa Xaa Arg Asn
1               5

<210> SEQ ID NO 55
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nva
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 55

Xaa Leu Xaa Xaa Arg Asn
1               5

<210> SEQ ID NO 56
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 56

Ile Leu Xaa Xaa Arg Asn
```

```
<210> SEQ ID NO 57
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: Nle
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 57

Xaa Leu Xaa Xaa Arg Asn
1               5

<210> SEQ ID NO 58
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 2-Cyclohexyl glycine
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 58

Xaa Leu Xaa Xaa Arg Asn
1               5

<210> SEQ ID NO 59
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 59

Xaa Leu Xaa Xaa Arg Asn
1               5

<210> SEQ ID NO 60
```

```
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 60

Thr Leu Xaa Xaa Arg Asn
1               5

<210> SEQ ID NO 61
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 61

Asn Leu Xaa Xaa Arg Asn
1               5

<210> SEQ ID NO 62
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nva
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 62

Leu Xaa Xaa Xaa Arg Asn
1               5

<210> SEQ ID NO 63
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
```

<223> OTHER INFORMATION: Homoproline

<400> SEQUENCE: 63

Leu Ile Xaa Xaa Arg Asn
1               5

<210> SEQ ID NO 64
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: Nle
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 64

Leu Xaa Xaa Xaa Arg Asn
1               5

<210> SEQ ID NO 65
<211> LENGTH: 6
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (2)..(2)
<223> OTHER INFORMATION: 2-Cyclohexyl glycine
<220> FEATURE:
<221> NAME/KEY: BINDING
<222> LOCATION: (3)..(3)
<223> OTHER INFORMATION: Orn
<220> FEATURE:
<221> NAME/KEY: BINDING
<222> LOCATION: (4)..(4)
<223> OTHER INFORMATION: Homoproline

<400> SEQUENCE: 65

Leu Xaa Xaa Xaa Arg Asn
1               5

<210> SEQ ID NO 66
<211> LENGTH: 7
<212> TYPE: PRT
<213> ORGANISM: Artificial Sequence
<220> FEATURE:
<223> OTHER INFORMATION: NMUR2 Selective Agonist
<220> FEATURE:
<221> NAME/KEY: BINDING
<222> LOCATION: (1)..(1)
<223> OTHER INFORMATION: 3-Cyclohexyl alanine
<220> FEATURE:
<221> NAME/KEY: BINDING
<222> LOCATION: (4)..(4)
<223> OTHER INFORMATION: Orn
<220> FEATURE:
<221> NAME/KEY: BINDING
<222> LOCATION: (5)..(5)
<223> OTHER INFORMATION: Homoproline

<400> SEQUENCE: 66

```
Xaa Leu Leu Xaa Xaa Arg Asn
1               5

<210> SEQ ID NO 67
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: BINDING
<222> LOCATION: (3)..(3)
<223> OTHER INFORMATION: Dpr

<400> SEQUENCE: 67

Leu Leu Xaa Pro Arg Asn
1               5

<210> SEQ ID NO 68
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: BINDING
<222> LOCATION: (3)..(3)
<223> OTHER INFORMATION: Dbu

<400> SEQUENCE: 68

Asp Leu Xaa Pro Arg Asn
1               5

<210> SEQ ID NO 69
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: BINDING
<222> LOCATION: (3)..(3)
<223> OTHER INFORMATION: Dbu

<400> SEQUENCE: 69

Leu Thr Xaa Pro Arg Asn
1               5

<210> SEQ ID NO 70
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: BINDING
<222> LOCATION: (2)..(2)
<223> OTHER INFORMATION: Dbu
<220> FEATURE:
<221> NAME/KEY: BINDING
<222> LOCATION: (3)..(3)
<223> OTHER INFORMATION: Dbu

<400> SEQUENCE: 70

Leu Xaa Xaa Pro Arg Asn
1               5

<210> SEQ ID NO 71
<211> LENGTH: 6
<212> TYPE: PRT
```

```
<213> ORGANISM: Artificial Sequence
<220> FEATURE:
<223> OTHER INFORMATION: Peptide
<220> FEATURE:
<221> NAME/KEY: BINDING
<222> LOCATION: (3)..(3)
<223> OTHER INFORMATION: Dbu

<400> SEQUENCE: 71

Leu Asn Xaa Pro Arg Asn
1               5

<210> SEQ ID NO 72
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: BINDING
<222> LOCATION: (3)..(3)
<223> OTHER INFORMATION: Dbu

<400> SEQUENCE: 72

Leu Asp Xaa Pro Arg Asn
1               5
```

PEPTIDE OR PHARMACEUTICALLY ACCEPTABLE SALT THEREOF, OR PRODRUG THEREOF

CROSS REFERENCE TO RELATED APPLICATION

This Application is a 371 of PCT/JP2018/001651 filed on Jan. 19, 2018 which, in turn, claimed the priority of Japanese Patent Application No. 2017-008301 filed on Jan. 20, 2017, both applications are incorporated herein by reference.

TECHNICAL FIELD

The present invention relates to a peptide or a pharmaceutically acceptable salt thereof, or a prodrug thereof.

BACKGROUND ART

Neuromedin U (NMU) is a physiologically active peptide having a function of suppressing food intake or boosting energy metabolism, increasing body temperature, reducing body weight, or the like, and is expected to be applied as an anti-obesity drug (Patent Literature 1 and Non Patent Literature 1). In addition, it recently becomes evident that neuromedin U is involved in the glucose homeostasis, and neuromedin U also receives attention as a pharmaceutical for treating diabetes (Non Patent Literature 2).

It is noted that the amidated C-terminal 7 residues ($Phe^1$-$Leu^2$-$Phe^3$-$Arg^4$-$Pro^5$-$Arg^6$-$Asn^7$-$NH_2$) of NMU, which has been identified from each animal, remain exactly the same in mammals and are believed to be important for the activation of type 1 and type 2 NMU receptors (NMUR1 and NMUR2). It is known that NMUR1 is mainly expressed at high level in the peripheral tissues (mainly, intestinal tract, lung, or the like) while NMUR2 is mainly expressed at high level in the central system (mainly, hypothalamic paraventricular nucleus). Due to this reason, a selective agonist is required for each of NMUR1 and NMUR2.

For example, in Non Patent Literature 3, 3-cyclohexyl-propionyl-$Leu^2$-$Leu^3$-$Dpr^4$-$Pro^5$-$Arg^6$-$Asn^7$-$NH_2$ (Dpr: 2,3-diaminopropionic acid) is disclosed as a peptide which selectively activates NMUR2.

CITATION LIST

Patent Literatures

Patent Literature 1: WO 2015/095719 A Non Patent Literatures

Non Patent Literatures 1: E. D. Micewiez, and 7 others, "Small lipidated anti-obesity compounds derived from neuromedin U", European Journal of Medical Chemistry (2015) 101, 616-626

Non Patent Literatures 2: P. Ingallinella, and 13 others, "PEGylation of neuromedin U yields a promising candidate for the treatment of obesity and diabetes", Bioorganic & Medical Chemistry (2012) 20, 4751-4759

Non Patent Literature 3: K. Takayama, and 8 others, "Discovery of selective hexapeptide agonists to human neuromedin U receptors types 1 and 2", Journal of Medicinal Chemistry (2014) 57, 6583-6593

SUMMARY OF INVENTION

NMUR2 can be selectively activated for sure by the peptide described in Non Patent Literature 3. However, the inventors of the present invention have found that the peptide described in Non Patent Literature 3 is chemically unstable under physiological conditions.

Therefore, the present invention was made in consideration of the above circumstances, and an object of the present invention is to provide a peptide that can selectively activate NMUR2 and is chemically stable under physiological conditions.

To solve the problems described above, the inventors of the present invention have conducted intensive studies. As a result, the inventors have found that the problems can be solved by a peptide represented by the following Formula (1) or a pharmaceutically acceptable salt thereof, or a prodrug thereof, and have completed the present invention accordingly.

[Chem. 1]

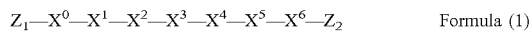

$$Z_1-X^0-X^1-X^2-X^3-X^4-X^5-X^6-Z_2 \qquad \text{Formula (1)}$$

In the above Formula (1), $X^0$ is an Ala residue which may have a substituent selected from the group consisting of an alicyclic group, an aromatic hydrocarbon group, an aralkyl group, and a heterocyclic group in a side chain, or is absent;

$X^1$ is an amino acid residue selected from the group consisting of Leu, Val, Ile, Thr, Asn, Gln, Ala, norvaline, isovaline, norleucine, 2-cyclohexylglycine, 3-cyclohexylalanine, 2,4-diaminobutanoic acid, 2,3-diaminopropionic acid, 2-aminobutyric acid, and 2-aminoisobutyric acid;

$X^2$ is an amino acid residue selected from the group consisting of Leu, Val, Ile, norvaline, norleucine, and 2-cyclohexylglycine;

$X^3$ is an amino acid residue selected from the group consisting of 2,4-diaminobutanoic acid, ornithine, 2-pyridylalanine, 3-pyridylalanine, and 4-pyridylalanine;

$X^4$ is a Pro residue or a homoproline residue;

$X^5$ is an Arg residue;

$X^6$ is an Asn residue;

$Z_1$ is a hydrogen atom or $R_1-(R_2)_n-CO-$; $R_1$ is a hydrogen atom or a hydroxy group, or a substituted or unsubstituted chain hydrocarbon group, alicyclic hydrocarbon group, aromatic hydrocarbon group, or heterocyclic group; $R_2$ is an alkylene group, an oxyalkylene group, or an alkyleneoxy group; and n is 0 or 1; and $Z_2$ is an amino group, a hydrogen atom, a hydroxy group, an alkoxy group, a hydrocarbon group, or a polyalkylene glycol group.

DESCRIPTION OF EMBODIMENTS

Figure 1:
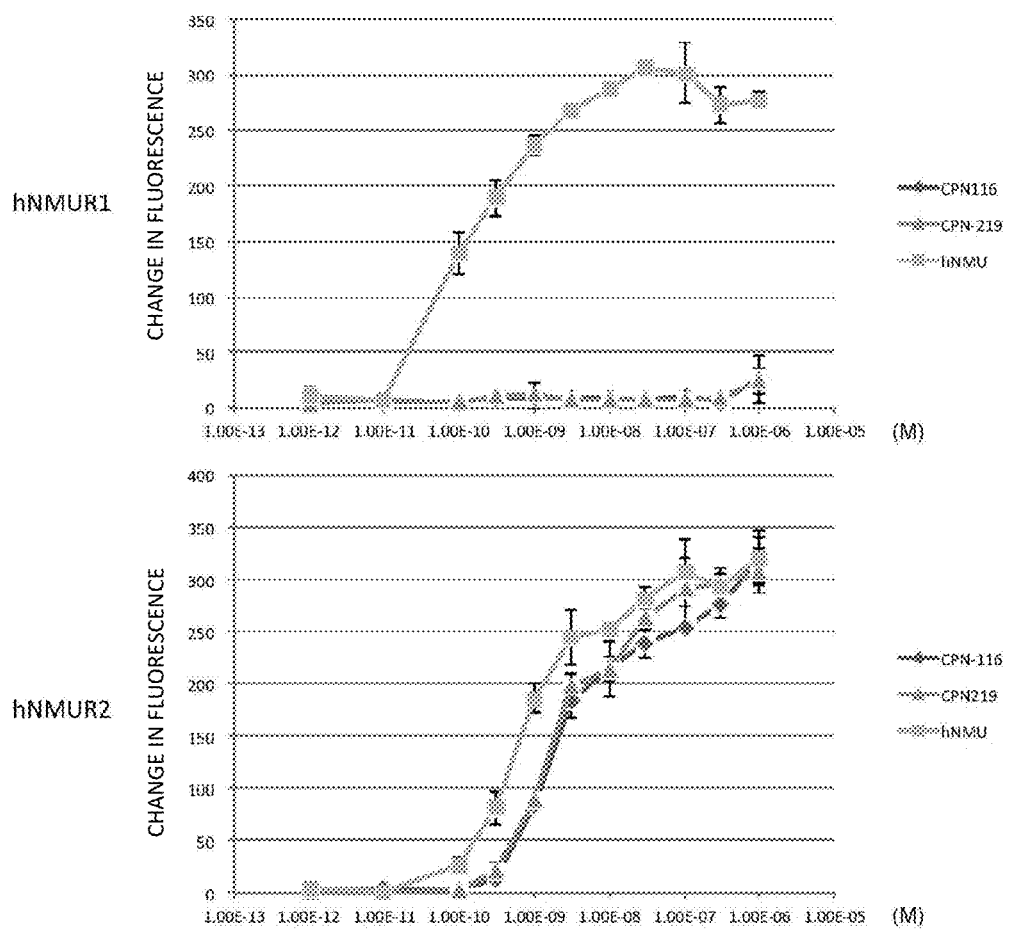
FIG. 1 illustrates the agonist activity for hNMUR1 and hNMUR2 by peptides of Examples and Comparative Examples.

As described above, the inventors of the present invention have found that the peptide described in Non Patent Literature 3 is chemically unstable under physiological conditions. Specifically, it is found that, in the peptide described in Non Patent Literature 3, the acyl group (3-cyclohexylpropionyl-Leu$^2$-Leu$^3$) transfer reaction between the α and β amino groups of Dpr$^4$ residue occurs under physiological conditions (chemical instability). The inventors of the present invention have further found that the agonist activity of the peptide derivative is lost as the acyl group is transferred to the β-position amino group of Dpr$^4$ residue. Furthermore, the inventors of the present invention have surprisingly found that, by converting Dpr$^4$ residue of the peptide described in Non Patent Literature 3 to a residue of 2,4-diaminobutanoic acid, an ornithine residue, a pyridylalanine residue, or the like, the peptide is chemically stabilized under physiological conditions.

Such a peptide can selectively activate NMUR2 and also can be present in a chemically stable state under physiological conditions.

Hereinbelow, embodiments of the present invention will be described. In addition, the present invention is not limited to the following embodiments only.

In the present specification, the expression "X to Y" representing a range means "not less than X and not more than Y". Furthermore, unless specifically described otherwise, operations and measurements of physical properties or the like are carried out under conditions of room temperature (20 to 25° C.)/relative humidity of 40 to 50% RH.

In the present specification, the "peptide represented by Formula (1) or a pharmaceutically acceptable salt thereof" is also simply referred to as a "peptide according to the present invention". Furthermore, the "type 2 neuromedin U receptor" is also simply referred to as "NMUR2" and "type 1 neuromedin U receptor" is also simply referred to as "NMUR1".

In the present specification, the expression "NMUR2 selective agonist" or "selectively activates NMUR2" means that the relative agonist activity for NMUR1 is 18% or less at 1000 nM and the relative agonist activity for NMUR2 is 48% or more at 100 nM.

The "amino acid residue" described in the present invention means, in a peptide or a protein molecule, a portion that corresponds to one unit of the amino acid constituting the peptide or protein. More specifically, the amino acid residue means a divalent group derived from an α-amino acid, as represented by the following Formula (2):
[Chem. 2]

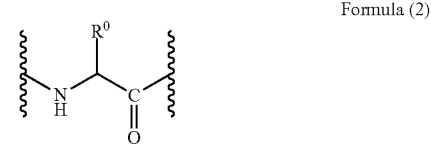

Formula (2)

Here, $R^0$ is a side chain of the amino acid, and for example, is a hydrogen atom for Gly, or a methyl group for Ala.

The "amino acid residue" is derived from a natural or non-natural α-amino acid, and in a case in which an optical isomer may be present, the amino acid residue can be any one of an L form and a D form, but is preferably an L form. More specifically, as for the "amino acid residue", Arg, Lys, Asp, Asn, Glu, Gln, His, Pro, Tyr, Trp, Ser, Thr, Gly, Ala, Met, Cys, Phe, Leu, Val, and Ile, and analogues thereof can be exemplified. As for the analogues, derivatives of the above 20 amino acid residues in which the side chain is substituted with any substituent are acceptable, and for example, halogenated derivatives of the above 20 amino acid residues (for example, 3-chloroalanine), 2-aminobutyric acid, norleucine, norvaline, isovaline, 2-aminoisobutyric acid, homophenylalanine, 2,3-diaminopropionic acid, 2,4-diaminobutanoic acid, ornithine, 2-hydroxyglycine, homoserine, hydroxylysine, hydroxyproline, 3,4-didehydroproline, homoproline, homocysteine, homomethionine, aspartic acid ester (for example, aspartic acid-methyl ester, aspartic acid-ethyl ester, aspartic acid-propyl ester, aspartic acid-cyclohexyl ester, aspartic acid-benzyl ester, or the like), glutamic acid ester (glutamic acid-cyclohexyl ester, glutamic acid-ethyl ester, glutamic acid-propyl ester, glutamic acid-methyl ester, glutamic acid-benzyl ester, or the like), and amino acid residues derived from an amino acid such as formyltryptophan, 2-cyclopentylglycine, 2-cyclohexylglycine, 2-phenylglycine, 2-pyridylalanine, 3-cyclopentylalanine, 3-cyclohexylalanine, 3-pyridylalanine, 3-pyrazolylalanine, 3-furanylalanine, 3-thienylalanine, methoxyphenylalanine, 3-naphthylalanine, and 4-pyridylalanin, or the like can be exemplified, but the analogues are not limited thereto. Furthermore, like Ile and Thr, for those having a diastereomer in which an asymmetric carbon is present in a side chain, the natural form (for example, (2R*,3R*)-2-amino-3-methylpentanoic acid and (2R*,3S*)-2-amino-3-hydroxybutanoic acid) and the non-natural form (for example, (2R*,3S*)-2-amino-3-methylpentanoic acid and (2R*, 3R*)-2-amino-3-hydroxybutanoic acid) can be used without any particular discrimination. Namely, "Ile" is used in the meaning to encompass both (2R*,3R*)-2-amino-3-methylpentanoic acid and (2R*,3S*)-2-amino-3-methylpentanoic acid, and "Thr" is used in the meaning to encompass both (2R*,3S*)-2-amino-3-hydroxybutanoic acid and (2R*,3R*)-2-amino-3-hydroxybutanoic acid. Preferably, a diastereomer of natural form (namely, for Ile, (2R*,3R*)-2-amino-3-methylpentanoic acid, and for Thr, (2R*,3S*)-2-amino-3-hydroxybutanoic acid) is used.

The amino acid sequence described in the present invention is, unless specifically mentioned otherwise, written in the N-terminus (amino terminal) to C-terminus (carboxyl terminal) direction according to custom.

It is known in the present technical field that respective amino acid residues may be substituted with amino acid residues having similar properties on the basis of a difference in the side chains thereof (conservative substitution). For example, Val, Leu, Ile, 2-aminobutyric acid (Abu), norleucine (Nle), norvaline (Nva), andisovaline (Iva) that are aliphatic hydrophobic amino acids may be substituted with each other. Gly, Ala, and 2-aminoisobutyric acid (Aib) of which side chain is a hydrogen atom or a methyl group may be substituted with each other. Asn and Gln that are neutral polar amino acids may be substituted with each other. 2,4-Diaminobutanoic acid (Dbu) and ornithine (Orn) may be substituted with each other. Pro and homoproline (homoPro) may be substituted with each other.

The "pharmaceutically acceptable salt" in the present specification is a metallic salt, an ammonium salt, an organic acid salt, an inorganic acid salt, or a salt with an organic base or an inorganic base that does not cause undesirable physiological effects after the administration to a patient or a subject. More specific examples thereof may include a sodium salt, a potassium salt, a calcium salt, a magnesium salt, a barium salt, an aluminum salt, a zinc salt, an ammonium salt, a methylamine salt, an ethylamine salt, an aniline salt, a dimethylamine salt, a diethylamine salt, apyrrolidine salt, a piperidine salt, a morpholine salt, a piperazine salt, a trimethylamine salt, a triethylamine salt, an ethanolamine salt, a diethanolamine salt, a triethanolamine salt, a hydrochloride salt, a hydrobromic acid salt, a nitrate salt, a sulfate salt, a phosphoric salt, a formate salt, an acetate salt, a trifluoroacetate salt, a phthalate salt, a fumarate salt, an oxalate salt, a tartrate salt, a maleate salt, a citric salt, a succinate salt, a malate salt, a methane sulfonate salt, a benzene sulfonate salt, a p-toluene sulfonate salt, and the like, but the pharmaceutically acceptable salt is not limited thereto.

A prodrug of the peptide according to the present invention (hereinbelow, the "prodrug of the peptide according to the present invention" is also simply referred to as "prodrug") indicates a peptide which converts into a peptide according to the present invention by having oxidation, reduction, hydrolysis, or the like as they are caused by gastric acid, an enzyme, or the like under physiological conditions in a living body. Those peptides can be produced from a peptide according to the present invention, for example, by a conventionally known method described in Bundgard, H., Design of Prodrugs, pp. 7-9, 21-24, Elsevier, Amsterdam 1985, or the like.

Examples of the prodrug in a case in which the side chain of an amino acid residue of the peptide according to the present invention has a carboxyl group may include ester derivatives obtained by reacting the carboxyl group with alcohol or amide derivatives obtained by reacting the carboxyl group with amine. More specific examples thereof include peptides in which the carboxyl group in the side chain of the peptide is derivatized by an ester represented by —COOR (R represents an alkyl group having 1 to 20 carbon atoms) or an amide group represented by —CONHR or —CONRR' (R and R' each independently represent an alkyl group having 1 to 20 carbon atoms).

Examples of the prodrug in a case in which the side chain of an amino acid residue of the peptide according to the present invention has a hydroxyl group may include acyloxy derivatives which are acylated by reacting the hydroxyl group with acid anhydride or the like. More specific examples thereof include peptides in which the hydroxyl group in the side chain of the peptide is derivatized by an acyloxy group represented by —OCOR (R represents an alkyl group having 1 to 20 carbon atoms).

Examples of the prodrug in a case in which the side chain of an amino acid residue of the peptide according to the present invention has an amino group may include derivatives in which the amino group is acylated, N-oxidized, alkylated, or phosphorylated. More specific examples thereof include peptides in which the amino group in the side chain is derivatized by an amide group represented by —NHCOR (R represents an alkyl group having 1 to 20 carbon atoms) or —NHCOCH(NH$_2$)CH$_3$.

In the present specification, the "substituent selected from the group consisting of an alicyclic group, an aromatic hydrocarbon group, a heterocyclic group, and an aralkyl group" for the amino acid or amino acid residue indicates a substituent in a side chain that is bonded to the α carbon of the amino acid or amino acid residue. The number of the substituents is generally 0 to 3, and preferably 0 to 1 per amino acid.

Examples of the alicyclic group may include alicyclic groups having 3 to 12 carbon atoms such as a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, and an adamantyl group, or the like, and the alicyclic group is preferably a cyclohexyl group.

The aromatic hydrocarbon group is a group derived from an aromatic hydrocarbon of a monocyclic or fused-ring structure, more specific examples thereof may include aromatic hydrocarbon groups having 6 to 20 carbon atoms such as a phenyl group, a naphthyl group, a tolyl group, and a phenanthryl group, or the like, and the aromatic hydrocarbon group is preferably a phenyl group or a naphthyl group.

Examples of the heterocyclic group may include substituents of a monocyclic, fused bicyclic, or fused tricyclic structure containing 1 to 3 hetero atoms selected from a nitrogen atom, an oxygen atom, and a sulfur atom in a ring, and more specific examples thereof may include a pyrrolidyl group, apyrrole group, apiperidyl group, apyridyl group, an imidazolyl group, a pyrazolyl group, an oxazolyl group, a thiazolyl group, a morpholyl group, an indolyl group, a benzimidazolyl group, a quinolyl group, a carbazolyl group, an oxetanyl group, a thietanyl group, a tetrahydrofuranyl group, a tetrahydrothienyl group, a furanyl group, a thienyl group, a tetrahydropyranyl group, a tetrahydrothiopyranyl group, or the like.

The aralkyl group is a group in which an alkyl group having 1 to 4 carbon atoms is substituted with an aromatic hydrocarbon group having 6 to 20 carbon atoms, and more specific examples thereof may include aralkyl groups having 7 to 24 carbon atoms such as a benzyl group, a phenethyl group, and a benzhydryl group.

The substituent of the amino acid or the amino acid residue may be further substituted with a substituent such as a linear or branched-chain alkyl group having 1 to 6 carbon atoms, a linear or branched-chain alkoxy group having 1 to 6 carbon atoms, a hydroxyl group, an amino group, a carboxyl group, an ester group, a carbamoyl group, an amide group, an acyl group, a nitro group, a sulfone group, a sulfonamide group, and/or halogen.

The amino acid or amino acid residue which is substituted with the substituent as described above is not particularly limited, but examples thereof may include 2-cyclopentylglycine, 2-cyclohexylglycine, 2-phenylglycine, 2-pyridylalanine, 3-cyclopentylalanine, 3-cyclohexylalanine, 3-pyridylalanine, 3-pyrazolylalanine, 3-furanylalanine, 3-thienylalanine, methoxyphenylalanine, 3-biphenylalanine, 3-(3-benzothienyl)-alanine, 3-naphthylalanine (for example, 3-(1-naphthyl)-alanine, 3-(2-naphthyl)-alanine), 4-pyridylalanine, and the like.

<Peptide>

According to one embodiment of the present invention, a peptide represented by the following Formula (1) or a pharmaceutically acceptable salt thereof, or a prodrug of the peptide and salt is provided:

[Chem. 3]

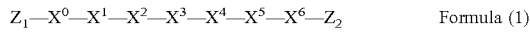

$$Z_1-X^0-X^1-X^2-X^3-X^4-X^5-X^6-Z_2 \quad \text{Formula (1)}$$

In the peptide according to the present invention, $X^0$ is an Ala residue which may have a substituent selected from the group consisting of an alicyclic group, an aromatic hydrocarbon group, an aralkyl group, and a heterocyclic group in a side chain, or is absent.

According to one embodiment of the present invention, from the viewpoint of the NMUR2 selective agonist activity, $X^0$ is preferably an Ala residue which is substituted with an alicyclic group, or is absent, and it is more preferably a 3-cyclohexylalanine residue or absent.

According to one embodiment of the present invention, from the viewpoint of the NMUR2 selective agonist activity, $X^0$ is absent.

In the peptide according to the present invention, $X^1$ is an amino acid residue selected from the group consisting of Leu, Val, Ile, Thr, Asn, Gln, Ala, norvaline, isovaline, norleucine, 2-cyclohexylglycine, 3-cyclohexylalanine, 2,4-diaminobutanoic acid, 2,3-diaminopropionic acid, 2-aminobutyric acid, and 2-aminoisobutyric acid.

From the viewpoint of the NMUR2 selective agonist activity, preferably, $X^1$ is an amino acid residue selected from the group consisting of Leu, Val, Ile, Thr, Asn, norvaline, norleucine, 2-cyclohexylglycine, 3-cyclohexylalanine, and 2,4-diaminobutanoic acid. More preferably, $X^1$ is an amino acid residue selected from the group consisting of Leu, Val, Ile, Thr, Asn, norvaline, norleucine, 2-cyclohexylglycine, and 3-cyclohexylalanine.

In the peptide according to the present invention, $X^2$ is an amino acid residue selected from the group consisting of Leu, Val, Ile, norvaline, isovaline, norleucine, and 2-cyclohexylglycine.

From the viewpoint of the NMUR2 selective agonist activity, preferably, $X^2$ is an amino acid residue selected from the group consisting of Leu, Val, Ile, norvaline, norleucine, and 2-cyclohexylglycine. More preferably, $X^2$ is an amino acid residue selected from the group consisting of Leu, Ile, norvaline, norleucine, and 2-cyclohexylglycine. Even more preferably, $X^2$ is an amino acid residue selected from Leu, norvaline, or norleucine.

In the peptide according to the present invention, $X^3$ is an amino acid residue selected from the group consisting of 2,4-diaminobutanoic acid, ornithine, 2-pyridylalanine, 3-pyridylalanine, and 4-pyridylalanine. As $X^3$ is selected from those amino acid residues, the chemical stability under physiological conditions is obtained while the NMUR2 selective agonist activity is maintained at high level.

$X^3$ is, from the viewpoint of the chemical stability under physiological conditions, preferably a residue of 2,4-diaminobutanoic acid or an ornithine residue. More preferably, $X^3$ is a residue of 2,4-diaminobutanoic acid.

In the peptide according to the present invention, $X^4$ is a Pro residue or a homoproline residue.

In the peptide according to the present invention, $X^5$ is an Arg residue.

In the peptide according to the present invention, $X^6$ is an Asn residue.

According to one embodiment of the present invention, in Formula (1), $X^0$ is a 3-cyclohexylalanine residue or absent; $X^1$ is an amino acid residue selected from the group consisting of Leu, Val, Ile, Thr, Asn, norvaline, norleucine, 2-cyclohexylglycine, 3-cyclohexylalanine, and 2,4-diaminobutanoic acid; $X^2$ is an amino acid residue selected from the group consisting of Leu, Val, Ile, norvaline, norleucine, and 2-cyclohexylglycine; $X^3$ is an amino acid residue selected from the group consisting of 2,4-diaminobutanoic acid, ornithine, 2-pyridylalanine, 3-pyridylalanine, and 4-pyridylalanine; $X^4$ is a Pro residue or a homoproline residue; $X^5$ is an Arg residue; and $X^6$ is an Asn residue.

According to a preferred embodiment of the present invention, from the viewpoint of the NMUR2 selective agonist activity, in Formula (1), $X^0$ is absent; $X^1$ is an amino acid residue selected from the group consisting of Leu, Val, Ile, Thr, Asn, norvaline, norleucine, 2-cyclohexylglycine, 3-cyclohexylalanine, and 2,4-diaminobutanoic acid; $X^2$ is an amino acid residue selected from the group consisting of Leu, Ile, norvaline, norleucine, and 2-cyclohexylglycine; $X^3$ is an amino acid residue selected from the group consisting of 2,4-diaminobutanoic acid, ornithine, 2-pyridylalanine, 3-pyridylalanine, and 4-pyridylalanine; $X^4$ is a Pro residue or a homoproline residue; $X^5$ is an Arg residue; and $X^6$ is an Asn residue.

According to a preferred embodiment of the present invention, from the viewpoint of the NMUR2 selective agonist activity, in Formula (1), $X^0$ is absent; $X^1$ is an amino acid residue selected from the group consisting of Leu, Val, Ile, Thr, Asn, norvaline, norleucine, 2-cyclohexylglycine, 3-cyclohexylalanine, and 2,4-diaminobutanoic acid; $X^2$ is an amino acid residue selected from the group consisting of Leu, Ile, norvaline, norleucine, and 2-cyclohexylglycine; $X^3$ is a residue of 2,4-diaminobutanoic acid or an ornithine residue; $X^4$ is a Pro residue or a homoproline residue; $X^5$ is an Arg residue; and $X^6$ is an Asn residue.

According to a more preferred embodiment of the present invention, from the viewpoint of the NMUR2 selective agonist activity, in Formula (1), $X^0$ is absent; $X^1$ is an amino acid residue selected from the group consisting of Leu, Val, Ile, Thr, Asn, norvaline, norleucine, 2-cyclohexylglycine, and 3-cyclohexylalanine; $X^2$ is an amino acid residue selected from the group consisting of Leu, Ile, norvaline, norleucine, and 2-cyclohexylglycine; $X^3$ is a residue of 2,4-diaminobutanoic acid or an ornithine residue; $X^4$ is a Pro residue or a homoproline residue; $X^5$ is an Arg residue; and $X^6$ is an Asn residue.

In the peptide according to the present invention, $Z_1$ indicates the N-terminal structure of a peptide according to the present invention. $Z_1$ is a hydrogen atom or $R_1-(R_2)_n-CO-$; $R_1$ is a hydrogen atom or a hydroxy group, or a substituted or unsubstituted chain hydrocarbon group, alicyclic hydrocarbon group, aromatic hydrocarbon group, or heterocyclic group; $R_2$ is an alkylene group, an oxyalkylene group, or an alkyleneoxy group; and n is 0 or 1.

With regard to $R_1$, as the chain hydrocarbon group, a chain hydrocarbon group having 1 to 18 carbon atoms such as a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group can be exemplified, and it is preferably a methyl group, an ethyl group, a propyl group, an isopropyl group, a butyl group, an isobutyl group, a t-butyl group, a pentyl group, or a hexyl group.

With regard to $R_1$, as the alicyclic hydrocarbon group, an alicyclic group having 3 to 12 carbon atoms such as a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, and an adamantyl group can be exemplified, and it is preferably a cyclopentyl group or a cyclohexyl group.

With regard to $R_1$, as the aromatic hydrocarbon group, the aromatic hydrocarbon group is a group derived from an aromatic hydrocarbon of a monocyclic or fused-ring structure, more specifically, an aromatic hydrocarbon group having 6 to 20 carbon atoms such as a phenyl group, a naphthyl group, a tolyl group, and a phenanthryl group can be exemplified, and it is preferably a phenyl group or a naphthyl group.

With regard to $R_1$, as the heterocyclic group, substituents having a monocyclic, fused bicyclic, or fused tricyclic structure including 1 to 3 hetero atoms selected from a nitrogen atom, an oxygen atom, and a sulfur atom in a ring can be exemplified, and more specifically, a pyrrolidyl group, a pyrrole group, a piperidyl group, a pyridyl group, an imidazolyl group, a pyrazolyl group, an oxazolyl group, a thiazolyl group, a morpholyl group, an indolyl group, a benzimidazolyl group, a quinolyl group, a carbazolyl group, an oxetanyl group, a thietanyl group, a tetrahydrofuranyl group, a tetrahydrothienyl group, a furanyl group, a thienyl group, a tetrahydropyranyl group, a tetrahydrothiopyranyl group, and the like can be exemplified.

Those chain hydrocarbon group, alicyclic hydrocarbon group, aromatic hydrocarbon group, and heterocyclic group may be substituted, and as the substituent, a linear or branched-chain alkyl group having 1 to 6 carbon atoms, a linear or branched-chain alkoxy group having 1 to 6 carbon atoms, a hydroxyl group, an amino group, a carboxyl group, an ester group, a carbamoyl group, an amide group, an acyl group, a nitro group, a sulfone group, a sulfonamide group, a halogen, and/or the like can be exemplified. The substituent is preferably a methyl group, a methoxy group, or a chlorine atom.

In a case in which n is 1, as for the alkylene group as $R_2$, an alkylene group having 1 to 3 carbon atoms such as a methylene group, an ethylene group, a trimethylene group, and a propylene group can be exemplified, and it is preferably an ethylene group or a trimethylene group.

With regard to the oxyalkylene group as $R_2$, an oxyalkylene group having 1 to 3 carbon atoms such as an oxymethylene group, an oxyethylene group, an oxytrimethylene group, and oxypropylene group can be exemplified, and it is preferably an oxymethylene group or an oxyethylene group.

With regard to the alkyleneoxy group as $R_2$, an alkyleneoxy group having 1 to 3 carbon atoms such as a methyleneoxy group, an ethyleneoxy group, a trimethyleneoxy group, and a propyleneoxy group can be exemplified.

According to a preferred embodiment of the present invention, $Z_1$ is, from the viewpoint of the NMUR2 selective agonist activity, as follows; $R_1$ is, either substituted or unsubstituted, an alicyclic hydrocarbon group having 3 to 12 carbon atoms or an aromatic hydrocarbon group having 6 to 20 carbon atoms; $R_2$ is an alkylene group having 1 to 3 carbon atoms, an oxyalkylene group having 1 to 3 carbon atoms, or an alkyleneoxy group having 1 to 3 carbon atoms; and n is 1.

According to a more preferred embodiment of the present invention, $Z_1$ is, from the viewpoint of the NMUR2 selective agonist activity, selected from the group consisting of a 3-cyclohexylpropionyl group, a 3-cyclopentylpropionyl group, a 4-cyclohexylbutanoyl group, a 3-(2-methoxyphenyl)propionyl group, a 3-(3-methoxyphenyl)propionyl group, a 3-(4-methoxyphenyl)propionyl group, a 3-(4-chlorophenyl)propionyl group, a 3-(4-methylphenyl)propionyl group, a 4-phenylbutanoyl group, a 3-phenoxypropionyl group, a 4-(4-methoxyphenyl)butanoyl group, a 2-naphthoxyacetyl group, and a 1-hexanoyl group.

In the peptide according to the present invention, $Z_2$ indicates the C-terminal structure of a peptide according to the present invention, and it is represented by —CO—$Z_2$. $Z_2$ is an amino group, a hydrogen atom, a hydroxy group, an alkoxy group, a hydrocarbon group, or a polyalkylene glycol group, and it is preferably an amino group.

The amino group as $Z_2$ is represented by —$NH_2$, —$NHR^{11}$, and $NR^{11}R^{12}$, and it is preferably —$NH_2$. As for $R^{11}$ and $R^{12}$, each independently, an alkyl group having 1 to 6 carbon atoms such as a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, a hexyl group, and a cyclohexyl group; an aryl group having 6 to 10 carbon atoms such as a phenyl group and a naphthyl; an aralkyl group having 7 to 18 carbon atoms such as a benzyl group, a phenethyl group, and a benzhydryl group; sugar such as glucose; a polyethylene glycol group which may be modified with an alkyl group having 1 to 6 carbon atoms (for example, a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, and a hexyl group), or the like can be exemplified.

In a case in which $Z_2$ is a hydroxy group, the C-terminal of a peptide may have a carboxyl group (—COOH) structure or a carboxylate group (—COO$^-$) structure.

As for the alkoxy group as $Z_2$, an alkoxy group having 1 to 6 carbon atoms such as a methoxy group, an ethoxy group, a propoxy group, an isopropoxy group, a butoxy group, a pentyloxy group, and a hexyloxy group can be exemplified.

As for the hydrocarbon group as $Z_2$, the same substituent as the above $R^{11}$ or $R^{12}$ can be exemplified.

As for the polyalkylene glycol group as $Z_2$, a polyalkylene glycol group having 1 to 4 carbon atoms such as a polymethylene glycol group, a polyethylene glycol group, a polypropylene glycol group, and a polybutylene glycol group can be exemplified, and it is preferably a polyethylene glycol group. The polyalkylene glycol group may be also modified with an alkyl group having 1 to 6 carbon atoms (for example, a methyl group, an ethyl group, a propyl group, an isopropyl group, a cyclopropyl group, a butyl group, an isobutyl group, a sec-butyl group, a tert-butyl group, an amyl group, an isoamyl group, a tert-amyl group, and a hexyl group). In addition, in the polyalkylene glycol group, the terminal may be substituted with an amino group.

With regard to the peptide according to the present invention, from the viewpoint of the NMUR2 selective agonist activity and chemical stability under physiological conditions, the peptide represented by Formula (1) includes any one of the amino acid sequences that are represented by SEQ ID NOs: 1 to 66.

More preferably, from the viewpoint of the NMUR2 selective agonist activity and chemical stability under physiological conditions, the peptide represented by Formula (1) includes any one of the amino acid sequences that are represented by SEQ ID NOs: 1 to 21. Even more preferably, the peptide represented by Formula (1) includes any one of the amino acid sequences that are represented by SEQ ID NOs: 1 to 12 and SEQ ID NOs: 14 to 21. Still even more preferably, the peptide represented by Formula (1) includes any one of the amino acid sequences that are represented by SEQ ID NOs: 1 to 10, SEQ ID NO: 12, and SEQ ID NOs: 14 to 18.

According to a preferred embodiment of the present invention, from the viewpoint of further enhancing the NMUR2 selective agonist activity and chemical stability under physiological conditions, the peptide according to the present invention is a peptide that is selected from the group consisting of the following Formula (1-1) to Formula (1-32).
[Chem. 4]

| | |
|---|---|
| 3-cyclohexylpropionyl-Leu-Leu-Dbu-Pro-Arg-Asn-NH$_2$ | Formula (1-1): |
| 3-cyclohexylpropionyl-Leu-Leu-Orn-Pro-Arg-Asn-NH$_2$ | Formula (1-2): |
| 3-cyclohexylpropionyl-Leu-Leu-Dbu-X$^4$-Arg-Asn-NH$_2$ (X$^4$: homoproline) | Formula (1-3): |
| 3-cyclopentylpropionyl-Leu-Leu-Dbu-Pro-Arg-Asn-NH$_2$ | Formula (1-4): |
| 4-cyclohexylbutanoyl-Leu-Leu-Dbu-Pro-Arg-Asn-NH$_2$ | Formula (1-5): |
| 3-(2-methoxyphenyl)propionyl-Leu-Leu-Dbu-Pro-Arg-Asn-NH$_2$ | Formula (1-6): |
| 3-(3-methoxyphenyl)propionyl-Leu-Leu-Dbu-Pro-Arg-Asn-NH$_2$ | Formula (1-7): |
| 3-(4-methoxyphenyl)propionyl-Leu-Leu-Dbu-Pro-Arg-Asn-NH$_2$ | Formula (1-8): |
| 3-(4-chlorophenyl)propionyl-Leu-Leu-Dbu-Pro-Arg-Asn-NH$_2$ | Formula (1-9): |
| 3-(4-methylphenyl)propionyl-Leu-Leu-Dbu-Pro-Arg-Asn-NH$_2$ | Formula (1-10): |
| 4-phenylbutanoyl-Leu-Leu-Dbu-Pro-Arg-Asn-NH$_2$ | Formula (1-11): |
| 3-phenoxypropionyl-Leu-Leu-Dbu-Pro-Arg-Asn-NH$_2$ | Formula (1-12): |
| 4-(4-methoxyphenyl)butanoyl-Leu-Leu-Dbu-Pro-Arg-Asn-NH$_2$ | Formula (1-13): |
| 2-naphthoxyacetyl-Leu-Leu-Dbu-Pro-Arg-Asn-NH$_2$ | Formula (1-14): |
| 3-cyclohexylpropionyl-Val-Leu-Dbu-Pro-Arg-Asn-NH$_2$ | Formula (1-15): |
| 3-cyclohexylpropionyl-Nva-Leu-Dbu-Pro-Arg-Asn-NH$_2$ | Formula (1-16): |
| 3-cyclohexylpropionyl-Ile-Leu-Dbu-Pro-Arg-Asn-NH$_2$ | Formula (1-17): |
| 3-cyclohexylpropionyl-Nle-Leu-Dbu-Pro-Arg-Asn-NH$_2$ | Formula (1-18): |
| 3-cyclohexylpropionyl-Chg-Leu-Dbu-Pro-Arg-Asn-NH$_2$ | Formula (1-19): |
| 3-cyclohexylpropionyl-Cha-Leu-Dbu-Pro-Arg-Asn-NH$_2$ | Formula (1-20): |
| 3-cyclohexylpropionyl-Thr-Leu-Dbu-Pro-Arg-Asn-NH$_2$ | Formula (1-21): |
| 3-cyclohexylpropionyl-Dbu-Leu-Dbu-Pro-Arg-Asn-NH$_2$ | Formula (1-22): |
| 3-cyclohexylpropionyl-Asn-Leu-Dbu-Pro-Arg-Asn-NH$_2$ | Formula (1-23): |
| 3-cyclohexylpropionyl-Leu-Val-Dbu-Pro-Arg-Asn-NH$_2$ | Formula (1-24): |
| 3-cyclohexylpropionyl-Leu-Nva-Dbu-Pro-Arg-Asn-NH$_2$ | Formula (1-25): |
| 3-cyclohexylpropionyl-Leu-Ile-Dbu-Pro-Arg-Asn-NH$_2$ | Formula (1-26): |
| 3-cyclohexylpropionyl-Leu-Nle-Dbu-Pro-Arg-Asn-NH$_2$ | Formula (1-27): |
| 3-cyclohexylpropionyl-Leu-Chg-Dbu-Pro-Arg-Asn-NH$_2$ | Formula (1-28): |
| 1-hexanoyl-Cha-Leu-Leu-Dbu-Pro-Arg-Asn-NH$_2$ | Formula (1-29): |
| 3-cyclohexylpropionyl-Leu-Leu-X$^3$-Pro-Arg-Asn-NH$_2$ (X$^3$: 2-pyridylalanine) | Formula (1-30): |
| 3-cyclohexylpropionyl-Leu-Leu-X$^3$-Pro-Arg-Asn-NH$_2$ (X$^3$: 3-pyridylalanine) | Formula (1-31): |
| 3-cyclohexylpropionyl-Leu-Leu-X$^3$-Pro-Arg-Asn-NH$_2$ (X$^3$: 4-pyridylalanine) | Formula (1-32): |

Dbu: 2,4-diaminobutanoic acid
Orn: ornithine
Nva: norvaline
Nle: norleucine
Chg: 2-cyclohexylglycine
Cha: 3-cyclohexylalanine <Method for Producing Peptide>

The peptide according to the present invention can be produced by conventionally known methods including a chemical synthesis method and a recombination technique. For preparing the peptide according to the present invention by chemical synthesis, the peptide can be produced by a method of usually using each amino acid in peptide chemistry, for example, a method described in "The Peptides" vol. 1 [written by Schroder and Luhke, Academic Press, New York, U.S.A. (1966)], "The basis and experiments in peptide syntheses" (written by Nobuo Izumiya et al., Maruzen, 1985), or the like, and the peptide can also be produced by any one of a liquid-phase method and a solid-phase method. Furthermore, any method of a column method and a batch method can also be used.

The peptide according to the present invention may also be produced, for example, by a method as described in the following Current Protocols in Molecular Biology, Chapter 16 or a recombination technique using animal cells, insect cells, microorganisms, or the like. The peptide is generated by cultured cells or microorganisms and then may be purified by a conventionally known method. The purification and isolation method of the peptide is known for a person who is skilled in the art, and can be performed, for example, by a method described in Current Protocols in Molecular Biology, Chapter 16 (written by Ausubel et al., John Wiley and Sons, 2006), or the like.

Examples of a condensation method for forming a peptide bond may include an azide method, an acid halide method, an acid anhydride method, a carbodiimide method, a carbodiimide-additive method, an active ester method, a carbonylimidazole method, an oxidation-reduction method, an enzyme method, a method using Woodward reagent K, HATU reagent, or Bop reagent, and the like. Furthermore, regarding the condensation reaction in the solid-phase method, among the above-described methods, an acid anhydride method, a carbodiimide method, and an active ester method are exemplified as main methods.

Furthermore, when the peptide chain is extended by the solid-phase method, a C-terminal amino acid is bonded to a support such as a resin that is not soluble to an organic solvent to be used. As such a resin, a resin into which a functional group is introduced in order to bond an amino acid to the resin, a resin in which a spacer is inserted between the resin and a functional group, or the like can also be used according to purpose. More specifically, for example, a halomethyl resin such as a chloromethyl resin, an oxymethyl resin, a 4-(oxymethyl)-phenylacetamidemethyl resin, a 4-(oxymethyl)-phenoxymethyl resin, a Rink amide resin, and the like can be exemplified. Furthermore, before performing those condensation reactions, a means for protecting a carboxyl group, an amino group, a hydroxyl group, an amidino group, or the like which are not involved in the condensation reaction can be carried out by a generally known means. Furthermore, conversely, a carboxyl group or an amino group that is directly involved in the condensation reaction can also be activated.

As a protective group used for a protection means of a functional group that is not involved in the condensation reaction of each unit, protection can be performed by a protective group usually used in organic chemistry, for example, a protective group described in "Protective Groups in Organic Synthesis (written by Greene, John Wiley & Sons, Inc. (1981))" or the like. More specific examples of a protective group of a carboxyl group may include various generally known protective groups such as methyl ester, ethyl ester, benzyl ester, p-nitrobenzyl ester, t-butyl ester, and cyclohexyl ester. Examples of a protective group of an amino group may include a benzyloxycarbonyl group, a t-butoxycarbonyl group, an isobornyloxycarbonyl group, a 9-fluorenylmethoxycarbonyl group (Fmoc group), and the like.

Examples of activated forms of carboxyl groups include an acid anhydride corresponding to the carboxyl group; azide; and an active ester with pentafluorophenol, 2,4-dinitrophenol, cyanomethyl alcohol, p-nitrophenol, N-hydroxysuccinimide, N-hydroxy-5-norbornene-2,3-dicarboximide, N-hydroxyphthalimide, 1-hydroxybenzotriazole, or the like. Examples of activated forms of amino groups may include amide phosphate corresponding to the amino group or the like.

The condensation reaction at the time of peptide synthesis is usually performed in a solvent. Examples of the solvent may include chloroform, dichloromethane, ethyl acetate, N,N-dimethyl formamide, dimethyl sulfoxide, pyridine, dioxane, tetrahydrofuran, N-methyl pyrrolidone, water, and methanol, or a mixture thereof. Furthermore, regarding the reaction temperature of the condensation reaction, the condensation reaction can be performed, similar to the usual case, in a range of −30° C. to 50° C.

Furthermore, the types of elimination reaction of the protective group in the production process of the peptide can be selected depending on the types of protective group to be used as long as the protective group can be eliminated without having an influence on a peptide bond. Examples thereof include an acid treatment with hydrogen chloride, hydrogen bromide, anhydrous hydrogen fluoride, methane sulfonic acid, trifluoromethane sulfonic acid, trifluoroacetic acid, a mixture thereof, or the like, an alkaline treatment with sodium hydroxide, potassium hydroxide, hydrazine, diethylamine, piperidine, or the like, a sodium treatment or reduction with palladium carbon in liquid ammonia, and a silylation treatment with trimethylsilyl triflate, trimethylsilyl bromide, or the like. Furthermore, in the protective group elimination reaction by the acid or silylation agent treatment described above, it is preferable to add a cation capturing agent such as anisole, phenol, cresol, thioanisole, or ethanedithiol from the viewpoint of efficiently performing the protective group elimination reaction.

Furthermore, a method for cutting the peptide of the present invention synthesized by a solid-phase method from the solid-phase is also performed according to a generally known method. For example, the above-described treatment using an acid or a silylation agent or the like can be exemplified as the cutting method. Generally known separation and purification means can be employed for the peptide of the present invention produced in this way after a series of reactions that are described in the above. For example, the peptide of the present invention can be obtained with a higher purity by extraction, distribution, reprecipitation, recrystallization, solid-phase extraction, column chromatography, or the like.

With regard to the peptide according to the present invention, modification of the N-terminal and C-terminal of a peptide can be carried out by a conventionally known method. The modification of the N-terminal can be achieved by, in a case in which the peptide is synthesized by a solid-phase method, introducing 3-cyclohexylpropionic acid or the like for modifying the N-terminal by the aforementioned $Z_1$ after deprotecting the final amino acid residue. Furthermore, for the modification of the C-terminal, amide form of the peptide can be obtained according to solid-phase synthesis using Rink amide resin, which is a resin for synthesizing amide form, for example.

The peptide according to the present invention may be isolated or purified. The expression "isolated or purified" means that an operation to remove components other than the target component has been applied. The purity of the isolated or purified peptide according to the present invention is usually 50% or higher (for example, 70% or higher, 80% or higher, 90% or higher, 95% or higher, 98% or higher, 99% or higher, or 1000).

<NMUR2 Selective Agonist Agent, Prophylactic/Therapeutic Agent, and Prophylactic/Therapeutic Method>

According to one embodiment of the present invention, a selective agonist agent for type 2 neuromedin U receptor which contains the peptide according to the present invention or a prodrug thereof (in the present specification, the "selective agonist agent for type 2 neuromedin U receptor which contains the peptide according to the present invention or a prodrug thereof" is also simply referred to as an "NMUR2 selective agonist agent") is provided.

One embodiment of the present invention is a peptide according to the present invention or a prodrug thereof used as a selective agonist for type 2 neuromedin U receptor.

One embodiment of the present invention is a method for selective activation of NMUR2 including administering an effective amount of a peptide according to the present invention or a prodrug thereof to a patient.

By administering an effective amount of the NMUR2 selective agonist agent to a subject, effects like suppressing food intake, boosting energy metabolism, increasing body temperature, reducing body weight, or the like can be achieved. The NMUR2 selective agonist agent may consist of one or more kinds of the peptide according to the present invention, or one or more kinds of a prodrug thereof, or a mixture of them. The NMUR2 selective agonist agent is, in general, a pharmaceutical composition which contains one or more kinds selected from the peptide according to the present invention and a prodrug thereof, and a pharmaceutically acceptable carrier.

According to one embodiment of the present invention, a prophylactic and/or therapeutic agent for metabolic syndrome, obesity, or diabetes containing the peptide according to the present invention and a prodrug thereof (in the present specification, the "prophylactic and/or therapeutic agent for metabolic syndrome, obesity, or diabetes containing the peptide according to the present invention and a prodrug thereof" is also simply referred to as a "prophylactic/therapeutic agent for obesity/diabetes") is provided. By administering an effective amount of the prophylactic/therapeutic agent for obesity/diabetes to a patient, effects like prevention and/or treatment of metabolic syndrome, obesity, or diabetes can be achieved based on the activity of suppressing food intake, boosting energy metabolism, increasing body temperature, reducing body weight, or the like. The prophylactic/therapeutic agent for obesity/diabetes may consist of one or more kinds of the peptide according to the present invention, or one or more kinds of a prodrug thereof, or a mixture of them. The prophylactic/therapeutic agent for obesity/diabetes is, in general, a pharmaceutical composition which contains one or more kinds selected from the peptide according to the present invention and a prodrug thereof, and a pharmaceutically acceptable carrier.

According to one embodiment of the present invention, the prophylactic/therapeutic agent for obesity/diabetes can be used such that it is administered to inside of a body.

According to one embodiment of the present invention, the prophylactic/therapeutic agent for obesity/diabetes can be used such that it is administered topically, preferably by intravenous, intranasal, or subcutaneous administration, and more preferably by intranasal administration.

The dose of the peptide according to the present invention or a prodrug thereof can be appropriately selected according to the administration subject, administration route, target disease, clinical symptoms, or the like. The dose is, in terms of a single dose, generally 5 µg to 100 mg/unit body weight, preferably 500 µg to 50 mg/unit body weight, and more preferably 1 to 10 mg/unit body weight. Furthermore, according to a study on preparation of a formulation, the dose can be reduced. The administration number per day is not particularly limited, and for example, it can be administered 1 to 3 times per day.

According to a preferred embodiment of the present invention, the prophylactic/therapeutic agent for obesity/diabetes, which is used such that the peptide according to the present invention or a prodrug thereof is administered in an amount of 1 to 10 mg/unit body weight to nasal cavity, is provided.

The peptide according to the present invention has NMUR2 selective agonist activity. Furthermore, the peptide according to the present invention is chemically stable under physiological conditions, for example, even in blood, and it has favorable pharmacokinetics of peptides in rats.

Thus, the prophylactic/therapeutic agent for obesity/diabetes of the present invention can exhibit, based on the favorable pharmacokinetics of peptides in rats, the activity of suppressing food intake, boosting energy metabolism, increasing body temperature, reducing body weight, or the like according to administration to a body, specifically, topical administration such as intravenous, intranasal, or subcutaneous administration, and the effects like prevention and/or treatment of metabolic syndrome, obesity, or diabetes can be achieved.

According to one embodiment of the present invention, a method for prevention and/or treatment of metabolic syndrome, obesity, or diabetes including administering an effective amount of a peptide according to the present invention or a prodrug thereof to a patient is provided. Furthermore, one embodiment of the present invention relates to a peptide according to the present invention or a prodrug thereof to be used for prevention and/or treatment of metabolic syndrome, obesity, or diabetes.

The metabolic syndrome indicates a condition like abdominal obesity, insulin resistance/hyperglycemia, abnormal lipid metabolism (hypertriglyceridemia, hypo-HDL-cholesterolemia), and blood pressure increase in which risk factors for having an occurrence of arteriosclerosis disorder and type II diabetes are integrated.

As for the obesity, obesity based on simple obesity, symptomatic obesity, a condition or a disorder accompanied with obesity, or the like can be exemplified, although it is not particularly limited thereto.

Examples of the symptomatic obesity may include endocrine obesity (Cushing's syndrome, hypothyroidism, insulinoma, obese type II diabetes, pseudohypoparathyroidism, hypogonadism, or the like); central obesity (hypothalamic obesity, frontal lobe syndrome, Kleine-Levin syndrome, or the like); hereditary obesity (Prader-Willi syndrome, Laurence-Moon-Biedl syndrome, or the like); drug-induced obesity (obesity due to steroid agent, phenothiazine, insulin, sulfonylurea (SU) agent, and β-blocker, or the like), or the like.

Examples of the condition or disease associated with obesity may include impaired glucose tolerance, diabetes (in particular, type II diabetes and obese diabetes, or the like), abnormal lipid metabolism (hypercholesterolemia, hyper-LDL-cholesterolemia, hypo-HDL-cholesterolemia, postprandial hyperlipidemia, hypertriglyceridemia, or the like), hypertension, heart failure, hyperuricemia/gout, fatty liver (including non-alchoholic steato-hepatitis), coronary artery disease (myocardial infarction, angina pectoris, or the like), cerebral infarction (cerebral thrombosis, transient ischemic attack, or the like), bone and joint disease (knee osteoarthritis, coxarthrosis, spondylosis deformans, lower back pain, or the like), sleep apnea syndrome/Pickwick syndrome, menstrual disorders (abnormal menstrual cycles, abnormal menstrual flow and cycle, amenorrhea, abnormal menstruation-related symptoms, or the like), metabolic syndrome, or the like.

As for the diabetes, the aforementioned type II diabetes, obese diabetes, or the like can be exemplified. Furthermore, complications of diabetes are also included in the diabetes. As for the complications, neuropathy, nephropathy, retinopathy, diabetic cardiomyopathy, cataract, macroangiopathy, osteopenia, hyperosmolar diabetic coma, infectious disease (respiratory infection, urinary tract infection, gastrointestinal infection, dermal soft tissue infection, inferior limb infection, or the like), diabetic gangrene, xerostomia, hypacusis, cerebrovascular disorder, peripheral blood circulation disorder, or the like can be exemplified.

According to one embodiment of the present invention, a prophylactic agent and/or a therapeutic agent for a prolactin secretion-related disorder containing the peptide according to the present invention or a prodrug thereof (in the present specification, the "prophylactic agent and/or a therapeutic agent for a prolactin secretion-related disorder containing the peptide according to the present invention or a prodrug thereof" is also simply referred to as a "prophylactic agent/therapeutic agent for a prolactin secretion-related disorder") is provided. By administering the prophylactic agent/therapeutic agent for a prolactin secretion-related disorder to a patient, secretion of prolactin can be controlled, in particular, excessive secretion of prolactin can be suppressed. As such, an effect like prevention and/or treatment of a prolactin secretion-related disorder can be achieved. The prophylactic agent/therapeutic agent for a prolactin secretion-related disorder may consist of one or more kinds of the peptide according to the present invention, or one or more kinds of a prodrug thereof, or a mixture of them. The prophylactic agent/therapeutic agent for a prolactin secretion-related disorder is, in general, a pharmaceutical composition which contains one or more kinds selected from the peptide according to the present invention and a prodrug thereof, and a pharmaceutically acceptable carrier.

One embodiment of the present invention relates to an agent for inhibiting prolactin secretion containing the peptide according to the present invention or a prodrug thereof.

According to one embodiment of the present invention, the prophylactic agent/therapeutic agent for a prolactin secretion-related disorder or agent for inhibiting prolactin secretion can be used such that they are administered to a body.

According to one embodiment of the present invention, the prophylactic agent/therapeutic agent for a prolactin secretion-related disorder or agent for inhibiting prolactin secretion can be used such that it is administered topically, preferably by intravenous, intranasal, or subcutaneous administration, and more preferably by intranasal administration.

The dose of the peptide according to the present invention or a prodrug thereof can be appropriately selected according to the administration subject, administration route, target disease, clinical symptoms, or the like. The dose is, in terms of a single dose, generally 5 μg to 100 mg/unit body weight, preferably 500 μg to 50 mg/unit body weight, and more preferably 1 to 10 mg/unit body weight. Furthermore, according to a study on preparation of a formulation, the dose can be reduced. The administration number per day is not particularly limited, and for example, it can be administered 1 to 3 times per day.

According to a preferred embodiment of the present invention, the prophylactic agent/therapeutic agent for a prolactin secretion-related disorder, which is used such that the peptide according to the present invention or a prodrug thereof is administered in an amount of 1 to 10 mg/unit body weight to nasal cavity, is provided.

As described in the above, the peptide according to the present invention has NMUR2 selective agonist activity. Furthermore, the peptide according to the present invention is chemically stable under physiological conditions, for example, even in blood, and it has favorable pharmacokinetics. Furthermore, the peptide according to the present invention or a prodrug thereof has an excellent brain delivery (for example, transfer into olfactory bulb).

It is believed accordingly that the prophylactic agent/therapeutic agent for a prolactin secretion-related disorder or agent for inhibiting prolactin secretion of the present invention can control, based on the favorable pharmacokinetics and brain delivery, the secretion of prolactin, in particular, can suppress excessive secretion of prolactin according to administration to a body, specifically, topical administration such as intravenous, intranasal, or subcutaneous administration.

According to one embodiment of the present invention, a method for prevention and/or treatment of a prolactin secretion-related disorder, including the peptide according to the present invention or a prodrug thereof, is provided. Furthermore, one embodiment of the present invention relates to the peptide according to the present invention or a prodrug thereof to be used for prevention and/or treatment of a prolactin secretion-related disorder.

The prolactin secretion-related disorder means a disorder accompanying excessive production of prolactin or a disorder having increased reactivity with prolactin. As for the prolactin secretion-related disorder, Parkinson syndrome, acromegaly, hypophyseal gigantism, pituitary adenoma with high prolactin in blood, prolactinoma, diencephalon tumor, ovulation disorder with high prolactin in blood, puerperal galactischia, galactorrhea, amenorrhea syndrome with galactorrhea, sterility, menstrual disorder, peripartum cardiomyopathy, restless leg syndrome, autoimmune disease, impotence, Chiari-Frommel syndrome, Argonz-del Castillo syndrome, Forbes-Albright syndrome, lymphoma, Sheehan's syndrome, spermatogenesis disorder, or the like can be exemplified. Among them, the prophylactic agent/therapeutic agent for a prolactin secretion-related disorder is preferably used for a disorder that is selected from the group consisting of Parkinson syndrome, acromegaly, hypophyseal gigantism, pituitary adenoma with high prolactin in blood, prolactinoma, diencephalon tumor, ovulation disorder with high prolactin in blood, puerperal galactischia, galactorrhea, amenorrhea syndrome with galactorrhea, sterility, menstrual disorder, peripartum cardiomyopathy, and restless leg syndrome.

In the present specification, the "effective dose" in the treatment is an amount that is appropriate in terms of a reasonable benefit/risk ratio and is effective for causing a certain desired therapeutic effect.

In the present specification, examples of the "subject" and the "patient" include humans and non-human animals including fishes, but preferably, they are selected from mammals such as humans, dogs, cats, mice, rats, hamsters, guinea pigs, horses (including racehorses), cattle, pigs, rabbits, and sheep, and domestic poultry such as chickens, quails, and turkeys, and more preferably humans.

The pharmaceutically acceptable carrier is not particularly limited, but examples thereof include vehicles such as lactose, sucrose, mannitol, starch, corn starch, crystalline cellulose, or light anhydrous silicate; lubricating agents such as silica, talc, calcium stearate, or magnesium stearate; binding agents such as hydroxypropyl cellulose, hydroxypropylmethyl cellulose, carboxymethyl cellulose, sodium carboxymethyl cellulose, methyl cellulose, polyvinyl pyrrolidone, crystalline cellulose, dextrin, or gelatin; antioxidizing agents such as ascorbic acid, sodium sulfite, sodium hydrogen sulfite, or tocopherol; chelating agents such as ethylenediamine tetraacetic acid (EDTA); buffers such as a borate salt, bicarbonate, Tris-HCl, a citric salt, a phosphoric salt, or other organic acids; solvents such as water for injection, physiological saline, ethanol, propanol, ethylene glycol, propylene glycol, macrogol, olive oil, or corn oil; surfactants or moistening agents such as Pluronic (registered trademark), polyethylene glycol, sorbitan fatty acid ester, polysorbate, Triton (registered trademark), lecithin, cholesterol, benzalkonium chloride, benzethonium chloride, or glycerine monostearate; isotonizing agents such as sodium chloride, potassium chloride, glycerine, dextrose, sorbitol, or mannitol; preserving agents such as benzoic acid, salicylic acid, thimerosal, phenethyl alcohol, methylparaben, propylparaben, or chlorohexidine; complexing agents; aminoacids; antifungus agents; colorants; flavoring agents and diluents; emulsifying agents; salt forming counter ions such as sodium; delivery vehicles; diluents; and the like (Remington's Pharmaceutical Sciences, 18th Edition, editorial supervisor: A. R. Gennaro, Mack Publishing Company, 1990).

The content of the peptide according to the present invention or a prodrug thereof in a pharmaceutical preparation may be 0.01 to 100% by weight with respect to the whole pharmaceutical preparation.

EMBODIMENTS

Hereinbelow, embodiments of the present invention are exemplified.

1. A peptide represented by a following Formula (1) or a pharmaceutically acceptable salt thereof, or a prodrug thereof:

[Chem. 5]

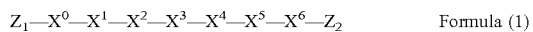

Formula (1)

in the above Formula (1), $X^0$ is an Ala residue which may have a substituent selected from the group consisting of an alicyclic group, an aromatic hydrocarbon group, an aralkyl group, and a heterocyclic group in a side chain, or is absent;

$X^1$ is an amino acid residue selected from the group consisting of Leu, Val, Ile, Thr, Asn, Gln, Ala, norvaline, isovaline, norleucine, 2-cyclohexylglycine, 3-cyclohexylalanine, 2,4-diaminobutanoic acid, 2,3-diaminopropionic acid, 2-aminobutyric acid, and 2-aminoisobutyric acid;

$X^2$ is an amino acid residue selected from the group consisting of Leu, Val, Ile, norvaline, isovaline, norleucine, and 2-cyclohexylglycine;

$X^3$ is an amino acid residue selected from the group consisting of 2,4-diaminobutanoic acid, ornithine, 2-pyridylalanine, 3-pyridylalanine, and 4-pyridylalanine;

$X^4$ is a Pro residue or a homoproline residue;

$X^5$ is an Arg residue;

$X^6$ is an Asn residue;

$Z_1$ is a hydrogen atom or $R_1$—$(R_2)_n$—CO—; $R_1$ is a hydrogen atom or a hydroxy group, or a substituted or unsubstituted chain hydrocarbon group, alicyclic hydrocarbon group, aromatic hydrocarbon group, or heterocyclic group; $R_2$ is an alkylene group, an oxyalkylene group, or an alkyleneoxy group; and n is 0 or 1; and $Z_2$ is an amino group, a hydrogen atom, a hydroxy group, an alkoxy group, a hydrocarbon group, or a polyalkylene glycol group.

2. The peptide or the pharmaceutically acceptable salt thereof described in above 1., in which the $X^0$ is a 3-cyclohexylalanine residue or absent.

3. The peptide, the pharmaceutically acceptable salt thereof, or the prodrug thereof described in above 1. or 2., in which in the $Z_1$, $R_1$ is a substituted or unsubstituted alicyclic group having 3 to 12 carbon atoms or aromatic hydrocarbon group having 6 to 20 carbon atoms; $R_2$ is an alkylene group having 1 to 3 carbon atoms, an oxyalkylene group having 1 to 3 carbon atoms, or an alkyleneoxy group having 1 to 3 carbon atoms; and n is 0.

4. The peptide, the pharmaceutically acceptable salt thereof, or the prodrug thereof described in any one of above 1. to 3., in which the $X^2$ is an amino acid residue selected from the group consisting of Leu, Ile, norvaline, norleucine, and 2-cyclohexylglycine.

5. The peptide, the pharmaceutically acceptable salt thereof, or the prodrug thereof described in any one of above 1. to 4., in which $X^3$ is a residue of 2,4-diaminobutanoic acid or an ornithine residue.

6. The peptide, the pharmaceutically acceptable salt thereof, or the prodrug thereof described in any one of above 1. to 5., in which the $X^1$ is an amino acid residue selected from the group consisting of Leu, Val, Ile, Thr, Asn, norvaline, norleucine, 2-cyclohexylglycine, and 3-cyclohexylalanine.

7. The peptide, the pharmaceutically acceptable salt thereof, or the prodrug thereof described in any one of above 1. to 3., in which the peptide represented by Formula (1) contains any one of the amino acid sequences that are represented by SEQ ID NOs: 1 to 66.

8. The peptide, the pharmaceutically acceptable salt thereof, or a prodrug thereof described in above 7, in which the peptide represented by Formula (1) contains any one of the amino acid sequences that are represented by SEQ ID NOs: 1 to 21.

9. A selective agonist agent for type 2 neuromedin U receptor containing the peptide, the pharmaceutically acceptable salt thereof, or the prodrug thereof described in any one of above 1. to 8.

10. A prophylactic and/or therapeutic agent for metabolic syndrome, obesity, or diabetes containing the peptide, the pharmaceutically acceptable salt thereof, or the prodrug thereof described in any one of above 1. to 8.

11. A method for prevention and/or treatment of metabolic syndrome, obesity, or diabetes including administering an effective amount of the peptide, the pharmaceutically acceptable salt thereof, or a prodrug thereof described in any one of above 1. to 8. to a patient.

12. A prophylactic agent and/or therapeutic agent for prolactin secretion-related disorder containing the peptide, the pharmaceutically acceptable salt thereof, or the prodrug thereof described in any one of above 1. to 8.

13. The prophylactic agent and/or therapeutic agent described in above 12., in which the prolactin secretion-related disorder is selected from the group consisting of Parkinson syndrome, acromegaly, hypophyseal gigantism, pituitary adenoma with high prolactin in blood, prolactinoma, diencephalon tumor, ovulation disorder with high prolactin in blood, puerperal galactischia, galactorrhea, amenorrhea syndrome with galactorrhea, sterility, menstrual disorder, peripartum cardiomyopathy, restless leg syndrome, autoimmune disease, impotence, Chiari-Frommel syndrome, Argonz-del Castillo syndrome, Forbes-Albright syndrome, lymphoma, Sheehan's syndrome, and spermatogenesis disorder.

14. A method for prevention and/or treatment of prolactin secretion-related disorder including administering an effective amount of the peptide, the pharmaceutically acceptable salt thereof, or the prodrug thereof described in any one of above 1. to 8. to a patient.

15. The method for prevention and/or treatment described in above 14., in which the prolactin secretion-related disorder is selected from the group consisting of Parkinson syndrome, acromegaly, hypophyseal gigantism, pituitary adenoma with high prolactin in blood, prolactinoma, diencephalon tumor, ovulation disorder with high prolactin in blood, puerperal galactischia, galactorrhea, amenorrhea syndrome with galactorrhea, sterility, menstrual disorder, peripartum cardiomyopathy, restless leg syndrome, autoimmune disease, impotence, Chiari-Frommel syndrome, Argonz-del Castillo syndrome, Forbes-Albright syndrome, lymphoma, Sheehan's syndrome, and spermatogenesis disorder.

EXAMPLES

Hereinbelow, effects of the present invention are explained by using the following Examples and Comparative Examples. However, the technical scope of the present invention is not limited to the following Examples.
<Synthesis of Peptide>

Synthesis Example 1

Synthesis of Peptide Containing the Amino Acid Sequence of SEQ ID NO: 1: CPN-219

3-Cyclohexylpropionyl-Leu-Leu-Dbu-Pro-Arg-Asn-NH$_2$ (CPN-219; Dbu: 2,4-diaminobutanoic acid)

CPN-219 was synthesized according to the Fmoc solid-phase peptide synthetic method that is described below.

75 mg (0.044 mmol) of Rink Amide resin (0.58 mmol/g, WATANABE CHEMICAL INDUSTRIES, LTD.) were weighed in a reaction vessel for Prelude 6 channel peptide synthesizer (Protein Technologies, Inc.), and set in the synthesizer. The following reactions were all carried out under nitrogen atmosphere. After the resin was swollen for 30 minutes at room temperature (25° C.) in dimethyl formamide (DMF) solution, by allowing the reaction to occur for 20 minutes at room temperature (25° C.) in 20% (v/v) piperidine/DMF solution (2.5 mL), Fmoc (9-fluorenylmethoxycarbonyl) group as a protective group on the resin was removed. The resin was washed 10 times with DMF (2.5 mL), and, in the presence of 34 mg (0.22 mmol, 5 eq.) of 1-hydroxybenzotriazole (HOBt) and 0.034 mL (0.22 mmol, 5 eq.) of N,N-diisopropylcarbodiimide (DIPCD), Fmoc-Asn(Trt)-OH (0.20 mmol, 5 eq.) was reacted at room temperature (25° C.) for 1 hour in DMF (1 mL) to introduce an amino acid onto the resin. In order to have condensation of the next amino acid, by allowing the reaction to occur for 20 minutes in 20% (v/v) piperidine/DMF solution (2.5 mL), Fmoc group on the resin was removed. Thereafter, in the same manner as the Fmoc-Asn(Trt)-OH, Fmoc-Arg(Pbf)-OH (0.22 mmol, 5 eq.), Fmoc-Pro-OH (0.22 mmol, 5 eq.), Fmoc-Dbu(Boc)-OH (0.22 mmol, 5 eq.), Fmoc-Leu-OH (0.22 mmol, 5 eq.), Fmoc-Leu-OH (0.22 mmol, 5 eq.), and 3-cyclohexylpropionic acid (0.22 mmol, 5 eq.) were introduced from the C-terminal side in sequence to extend the peptide chain. After the mixture was washed with DMF (2.5 mL, 6 times) and methanol (2.5 mL, 3 times), and diethyl ether (2.5 mL, 3 times), the resin was dried by purging with nitrogen. For removing various side chain-protecting groups and the resin removal, the reaction was allowed to occur for 2 hours in 5.0 mL of trifluoroacetic acid (TFA) in the presence of m-cresol (0.125 mL), thioanisole (0.125 mL), and 1,2-ethane dithiol (0.050 mL). By using a lot attached with glass filter, the resin was removed by filter filtration. After that, TFA was removed by distillation according to nitrogen spray, and crude peptide was precipitated by adding 40 mL of diethyl ether. The crude peptide was dissolved in 1M acetic acid and purified by high performance liquid chromatography to obtain a white solid (39.9 mg, yield 79%).

HRMS (ES+) calcd for (M$^+$+H) 849.5674, found 849.5676.

Synthesis Example 2

Synthesis of Peptide Containing the Amino Acid Sequence of SEQ ID NO: 2: CPN-221

3-Cyclohexylpropionyl-Leu-Leu-Orn-Pro-Arg-Asn-NH$_2$ (CPN-221; Orn: ornithine)

CPN-221 was synthesized and purified in the same manner as Synthesis Example 1 by using 75 mg (0.044 mmol) of Rink Amide resin (0.58 mmol/g, WATANABE CHEMICAL INDUSTRIES, LTD.) (32.8 mg, yield 650).

HRMS (ES+) calcd for (M$^+$+H) 863.5831, found 863.5829.

Synthesis Example 3

Synthesis of Peptide Containing the Amino Acid Sequence of SEQ ID NO: 3: CPN-227

3-Cyclohexylpropionyl-Leu-Leu-Dbu-homoPro-Arg-Asn-NH$_2$ (CPN-227; homoPro: homoproline)

CPN-227 was synthesized and purified in the same manner as Synthesis Example 1 by using 75 mg (0.044 mmol) of Rink Amide resin (0.58 mmol/g, WATANABE CHEMICAL INDUSTRIES, LTD.) (21.2 mg, yield 440).

HRMS (ES+) calcd for (M$^+$+H) 863.5831, found 863.5831.

Synthesis Example 4

Synthesis of Peptide Containing the Amino Acid Sequence of SEQ ID NO: 1: CPN-228

3-Cyclopentylpropionyl-Leu-Leu-Dbu-Pro-Arg-Asn-NH$_2$ (CPN-228)

CPN-228 was synthesized and purified in the same manner as Synthesis Example 1 by using 75 mg (0.044 mmol) of Rink Amide resin (0.58 mmol/g, WATANABE CHEMICAL INDUSTRIES, LTD.) (12.4 mg, yield 260).

HRMS (ES+) calcd for (M$^+$+H) 835.5518, found 835.5530.

Synthesis Example 5

Synthesis of Peptide Containing the Amino Acid Sequence of SEQ ID NO: 1: CPN-229

4-Cyclohexylbutanoyl-Leu-Leu-Dbu-Pro-Arg-Asn-NH$_2$ (CPN-229)

CPN-229 was synthesized and purified in the same manner as Synthesis Example 1 by using 75 mg (0.044 mmol) of Rink Amide resin (0.58 mmol/g, WATANABE CHEMICAL INDUSTRIES, LTD.) (13.2 mg, yield 270).

HRMS (ES+) calcd for (M$^+$+H) 863.5831, found 863.5838.

Synthesis Example 6

Synthesis of Peptide Containing the Amino Acid Sequence of SEQ ID NO: 1: CPN-230

3-(2-Methoxyphenyl)propionyl-Leu-Leu-Dbu-Pro-Arg-Asn-NH$_2$ (CPN-230)

CPN-230 was synthesized and purified in the same manner as Synthesis Example 1 by using 75 mg (0.044 mmol) of Rink Amide resin (0.58 mmol/g, WATANABE CHEMICAL INDUSTRIES, LTD.) (8.5 mg, yield 180).
HRMS (ES+) calcd for (M$^+$+H) 873.5310, found 873.5308.

Synthesis Example 7

Synthesis of Peptide Containing the Amino Acid Sequence of SEQ ID NO: 1: CPN-231

3-(3-Methoxyphenyl)propionyl-Leu-Leu-Dbu-Pro-Arg-Asn-NH$_2$ (CPN-231)

CPN-231 was synthesized and purified in the same manner as Synthesis Example 1 by using 75 mg (0.044 mmol) of Rink Amide resin (0.58 mmol/g, WATANABE CHEMICAL INDUSTRIES, LTD.) (11.6 mg, yield 240).
HRMS (ES+) calcd for (M$^+$+H) 873.5310, found 873.5309.

Synthesis Example 8

Synthesis of Peptide Containing the Amino Acid Sequence of SEQ ID NO: 1: CPN-232

3-(4-Methoxyphenyl)propionyl-Leu-Leu-Dbu-Pro-Arg-Asn-NH$_2$ (CPN-232)

CPN-232 was synthesized and purified in the same manner as Synthesis Example 1 by using 75 mg (0.044 mmol) of Rink Amide resin (0.58 mmol/g, WATANABE CHEMICAL INDUSTRIES, LTD.) (14.6 mg, yield 300).
HRMS (ES+) calcd for (M$^+$+H) 873.5310, found 873.5309.

Synthesis Example 9

Synthesis of Peptide Containing the Amino Acid Sequence of SEQ ID NO: 1: CPN-233

3-(4-Chlorophenyl)propionyl-Leu-Leu-Dbu-Pro-Arg-Asn-NH$_2$ (CPN-233)

CPN-233 was synthesized and purified in the same manner as Synthesis Example 1 by using 75 mg (0.044 mmol) of Rink Amide resin (0.58 mmol/g, WATANABE CHEMICAL INDUSTRIES, LTD.) (14.7 mg, yield 300).
HRMS (ES+) calcd for (M$^+$+H) 877.4815, found 877.4824.

Synthesis Example 10

Synthesis of Peptide Containing the Amino Acid Sequence of SEQ ID NO: 1: CPN-234

3-(4-Methylphenyl)propionyl-Leu-Leu-Dbu-Pro-Arg-Asn-NH$_2$ (CPN-234)

CPN-234 was synthesized and purified in the same manner as Synthesis Example 1 by using 75 mg (0.044 mmol) of Rink Amide resin (0.58 mmol/g, WATANABE CHEMICAL INDUSTRIES, LTD.) (9.2 mg, yield 190).
HRMS (ES+) calcd for (M$^+$+H) 857.5361, found 857.5354.

Synthesis Example 11

Synthesis of Peptide Containing the Amino Acid Sequence of SEQ ID NO: 1: CPN-235

4-Phenylbutanoyl-Leu-Leu-Dbu-Pro-Arg-Asn-NH$_2$ (CPN-235)

CPN-235 was synthesized and purified in the same manner as Synthesis Example 1 by using 75 mg (0.044 mmol) of Rink Amide resin (0.58 mmol/g, WATANABE CHEMICAL INDUSTRIES, LTD.) (6.9 mg, yield 140).
HRMS (ES+) calcd for (M$^+$+H) 857.5361, found 857.5355.

Synthesis Example 12

Synthesis of Peptide Containing the Amino Acid Sequence of SEQ ID NO: 1: CPN-236

3-Phenoxypropionyl-Leu-Leu-Dbu-Pro-Arg-Asn-NH$_2$ (CPN-236)

CPN-236 was synthesized and purified in the same manner as Synthesis Example 1 by using 75 mg (0.044 mmol) of Rink Amide resin (0.58 mmol/g, WATANABE CHEMICAL INDUSTRIES, LTD.) (16.3 mg, yield 340).
HRMS (ES+) calcd for (M$^+$+H) 859.5154, found 859.5163.

Synthesis Example 13

Synthesis of Peptide Containing the Amino Acid Sequence of SEQ ID NO: 1: CPN-237

4-(4-Methoxyphenyl)butanoyl-Leu-Leu-Dbu-Pro-Arg-Asn-NH$_2$ (CPN-237)

CPN-237 was synthesized and purified in the same manner as Synthesis Example 1 by using 75 mg (0.044 mmol) of Rink Amide resin (0.58 mmol/g, WATANABE CHEMICAL INDUSTRIES, LTD.) (14.7 mg, yield 300).
HRMS (ES+) calcd for (M$^+$+H) 887.5467, found 887.5473.

Synthesis Example 14

Synthesis of Peptide Containing the Amino Acid Sequence of SEQ ID NO: 1: CPN-238

2-Naphthoxyacetyl-Leu-Leu-Dbu-Pro-Arg-Asn-NH$_2$ (CPN-238)

CPN-238 was synthesized and purified in the same manner as Synthesis Example 1 by using 75 mg (0.044 mmol) of Rink Amide resin (0.58 mmol/g, WATANABE CHEMICAL INDUSTRIES, LTD.) (14.2 mg, yield 290).

HRMS (ES+) calcd for (M⁺+H) 895.5154, found 895.5153.

Synthesis Example 15

Synthesis of Peptide Containing the Amino Acid Sequence of SEQ ID NO: 4: CPN-239

3-Cyclohexylpropionyl-Val-Leu-Dbu-Pro-Arg-Asn-NH$_2$ (CPN-239)

CPN-239 was synthesized and purified in the same manner as Synthesis Example 1 by using 75 mg (0.044 mmol) of Rink Amide resin (0.58 mmol/g, WATANABE CHEMICAL INDUSTRIES, LTD.) (25.0 mg, yield 530).

HRMS (ES+) calcd for (M⁺+H) 835.5518, found 835.5530.

Synthesis Example 16

Synthesis of Peptide Containing the Amino Acid Sequence of SEQ ID NO: 5: CPN-240

3-Cyclohexylpropionyl-Nva-Leu-Dbu-Pro-Arg-Asn-NH$_2$ (CPN-240; Nva: norvaline)

CPN-240 was synthesized and purified in the same manner as Synthesis Example 1 by using 75 mg (0.044 mmol) of Rink Amide resin (0.58 mmol/g, WATANABE CHEMICAL INDUSTRIES, LTD.) (35.0 mg, yield 750).

HRMS (ES+) calcd for (M⁺+H) 835.5518, found 835.5519.

Synthesis Example 17

Synthesis of Peptide Containing the Amino Acid Sequence of SEQ ID NO: 6: CPN-241

3-Cyclohexylpropionyl-Ile-Leu-Dbu-Pro-Arg-Asn-NH$_2$ (CPN-241)

CPN-241 was synthesized and purified in the same manner as Synthesis Example 1 by using 75 mg (0.044 mmol) of Rink Amide resin (0.58 mmol/g, WATANABE CHEMICAL INDUSTRIES, LTD.) (30.0 mg, yield 630).

HRMS (ES+) calcd for (M⁺+H) 849.5674, found 849.5677.

Synthesis Example 18

Synthesis of Peptide Containing the Amino Acid Sequence of SEQ ID NO: 7: CPN-242

3-Cyclohexylpropionyl-Nle-Leu-Dbu-Pro-Arg-Asn-NH$_2$ (CPN-242; Nle: norleucine)

CPN-242 was synthesized and purified in the same manner as Synthesis Example 1 by using 75 mg (0.044 mmol) of Rink Amide resin (0.58 mmol/g, WATANABE CHEMICAL INDUSTRIES, LTD.) (30.9 mg, yield 650).

HRMS (ES+) calcd for (M⁺+H) 849.5674, found 849.5682.

Synthesis Example 19

Synthesis of Peptide Containing the Amino Acid Sequence of SEQ ID NO: 8: CPN-243

3-Cyclohexylpropionyl-Chg-Leu-Dbu-Pro-Arg-Asn-NH$_2$ (CPN-243; Chg: 2-cyclohexylglycine)

CPN-243 was synthesized and purified in the same manner as Synthesis Example 1 by using 75 mg (0.044 mmol) of Rink Amide resin (0.58 mmol/g, WATANABE CHEMICAL INDUSTRIES, LTD.) (30.6 mg, yield 630).

HRMS (ES+) calcd for (M⁺+H) 875.5831, found 875.5843.

Synthesis Example 20

Synthesis of Peptide Containing the Amino Acid Sequence of SEQ ID NO: 9: CPN-244

3-Cyclohexylpropionyl-Cha-Leu-Dbu-Pro-Arg-Asn-NH$_2$ (CPN-244; Cha: 3-cyclohexylalanine)

CPN-244 was synthesized and purified in the same manner as Synthesis Example 1 by using 75 mg (0.044 mmol) of Rink Amide resin (0.58 mmol/g, WATANABE CHEMICAL INDUSTRIES, LTD.) (30.0 mg, yield 610).

HRMS (ES+) calcd for (M⁺+H) 889.5987, found 889.5991.

Synthesis Example 21

Synthesis of Peptide Containing the Amino Acid Sequence of SEQ ID NO: 10: CPN-245

3-Cyclohexylpropionyl-Thr-Leu-Dbu-Pro-Arg-Asn-NH$_2$ (CPN-245)

CPN-245 was synthesized and purified in the same manner as Synthesis Example 1 by using 75 mg (0.044 mmol) of Rink Amide resin (0.58 mmol/g, WATANABE CHEMICAL INDUSTRIES, LTD.) (29.3 mg, yield 630).

HRMS (ES+) calcd for (M⁺+H) 837.5310, found 837.5311.

Synthesis Example 22

Synthesis of Peptide Containing the Amino Acid Sequence of SEQ ID NO: 11: CPN-246

3-Cyclohexylpropionyl-Dbu-Leu-Dbu-Pro-Arg-Asn-NH$_2$ (CPN-246)

CPN-246 was synthesized and purified in the same manner as Synthesis Example 1 by using 75 mg (0.044 mmol) of Rink Amide resin (0.58 mmol/g, WATANABE CHEMICAL INDUSTRIES, LTD.) (47.7 mg, yield 840).

HRMS (ES+) calcd for (M⁺+H) 836.5470, found 836.5474.

Synthesis Example 23

Synthesis of Peptide Containing the Amino Acid Sequence of SEQ ID NO: 12: CPN-247

3-Cyclohexylpropionyl-Asn-Leu-Dbu-Pro-Arg-Asn-NH$_2$ (CPN-247)

CPN-247 was synthesized and purified in the same manner as Synthesis Example 1 by using 75 mg (0.044 mmol) of Rink Amide resin (0.58 mmol/g, WATANABE CHEMICAL INDUSTRIES, LTD.) (35.7 mg, yield 750).

HRMS (ES+) calcd for (M⁺+H) 850.5263, found 850.5260.

Synthesis Example 24

Synthesis of Peptide Containing the Amino Acid Sequence of SEQ ID NO: 13: CPN-249

3-Cyclohexylpropionyl-Leu-Val-Dbu-Pro-Arg-Asn-NH$_2$ (CPN-249)

CPN-249 was synthesized and purified in the same manner as Synthesis Example 1 by using 75 mg (0.044 mmol) of Rink Amide resin (0.58 mmol/g, WATANABE CHEMICAL INDUSTRIES, LTD.) (34.4 mg, yield 740).

HRMS (ES+) calcd for (M⁺+H) 835.5518, found 835.5516.

Synthesis Example 25

Synthesis of Peptide Containing the Amino Acid Sequence of SEQ ID NO: 14: CPN-250

3-Cyclohexylpropionyl-Leu-Nva-Dbu-Pro-Arg-Asn-NH$_2$ (CPN-250)

CPN-250 was synthesized and purified in the same manner as Synthesis Example 1 by using 75 mg (0.044 mmol) of Rink Amide resin (0.58 mmol/g, WATANABE CHEMICAL INDUSTRIES, LTD.) (19.1 mg, yield 410).

HRMS (ES+) calcd for (M⁺+H) 835.5518, found 835.5522.

Synthesis Example 26

Synthesis of Peptide Containing the Amino Acid Sequence of SEQ ID NO: 15: CPN-251

3-Cyclohexylpropionyl-Leu-Ile-Dbu-Pro-Arg-Asn-NH$_2$ (CPN-251)

CPN-251 was synthesized and purified in the same manner as Synthesis Example 1 by using 75 mg (0.044 mmol) of Rink Amide resin (0.58 mmol/g, WATANABE CHEMICAL INDUSTRIES, LTD.) (21.8 mg, yield 460).

HRMS (ES+) calcd for (M⁺+H) 849.5674, found 849.5673.

Synthesis Example 27

Synthesis of Peptide Containing the Amino Acid Sequence of SEQ ID NO: 16: CPN-252

3-Cyclohexylpropionyl-Leu-Nle-Dbu-Pro-Arg-Asn-NH$_2$ (CPN-252)

CPN-252 was synthesized and purified in the same manner as Synthesis Example 1 by using 75 mg (0.044 mmol) of Rink Amide resin (0.58 mmol/g, WATANABE CHEMICAL INDUSTRIES, LTD.) (27.9 mg, yield 590).

HRMS (ES+) calcd for (M⁺+H) 849.5674, found 849.5671.

Synthesis Example 28

Synthesis of Peptide Containing the Amino Acid Sequence of SEQ ID NO: 17: CPN-253

3-Cyclohexylpropionyl-Leu-Chg-Dbu-Pro-Arg-Asn-NH$_2$ (CPN-253)

CPN-253 was synthesized and purified in the same manner as Synthesis Example 1 by using 75 mg (0.044 mmol) of Rink Amide resin (0.58 mmol/g, WATANABE CHEMICAL INDUSTRIES, LTD.) (18.8 mg, yield 390).

HRMS (ES+) calcd for (M⁺+H) 875.5831, found 875.5831.

Synthesis Example 29

Synthesis of Peptide Containing the Amino Acid Sequence of SEQ ID NO: 18: CPN-272

1-Hexanoyl-Cha-Leu-Leu-Dbu-Pro-Arg-Asn-NH$_2$ (CPN-272)

CPN-272 was synthesized and purified in the same manner as Synthesis Example 1 by using 75 mg (0.044 mmol) of Rink Amide resin (0.58 mmol/g, WATANABE CHEMICAL INDUSTRIES, LTD.) (33.4 mg, yield 64%).

HRMS (ES+) calcd for (M⁺+H) 962.6515, found 962.6522.

Synthesis Example 30

Synthesis of Peptide Containing the Amino Acid Sequence of SEQ ID NO: 19: CPN-302

3-Cyclohexylpropionyl-Leu-Leu-Ala(2-Pyri)-Pro-Arg-Asn-NH$_2$ (CPN-302; Ala(2-Pyri): 2-pyridylalanine)

CPN-302 was synthesized and purified in the same manner as Synthesis Example 1 by using 75 mg (0.044 mmol) of Rink Amide resin (0.58 mmol/g, WATANABE CHEMICAL INDUSTRIES, LTD.) (6.1 mg, yield 12%).

HRMS (ES+) calcd for (M⁺+H) 897.5674, found 897.5673.

Synthesis Example 31

Synthesis of Peptide Containing the Amino Acid Sequence of SEQ ID NO: 20: CPN-303

3-Cyclohexylpropionyl-Leu-Leu-Ala(3-Pyri)-Pro-Arg-Asn-NH$_2$ (CPN-303; Ala(3-Pyri): 3-pyridylalanine)

CPN-303 was synthesized and purified in the same manner as Synthesis Example 1 by using 75 mg (0.044 mmol) of Rink Amide resin (0.58 mmol/g, WATANABE CHEMICAL INDUSTRIES, LTD.) (37.4 mg, yield 74%).

HRMS (ES+) calcd for (M⁺+H) 897.5674, found 897.5677.

Synthesis Example 32

Synthesis of Peptide Containing the Amino Acid Sequence of SEQ ID NO: 21: CPN-304

3-Cyclohexylpropionyl-Leu-Leu-Ala(4-Pyri)-Pro-Arg-Asn-NH₂

(CPN-304; Ala(4-Pyri): 4-pyridylalanine)
CPN-304 was synthesized and purified in the same manner as Synthesis Example 1 by using 75 mg (0.044 mmol) of Rink Amide resin (0.58 mmol/g, WATANABE CHEMICAL INDUSTRIES, LTD.) (40.2 mg, yield 80%).
HRMS (ES+) calcd for (M⁺+H) 897.5674, found 897.5673.

Synthesis Example 33

Synthesis of Peptide Containing the Amino Acid Sequence of SEQ ID NO: 67 (Comparative Example): CPN-220

3-Cyclohexylpropionyl-Leu-Leu-Dpr-Pro-Arg-Asn-NH₂ (CPN-220; Dpr: 2,3-diaminopropionic acid)

The structure of CPN-220 is shown by the following formula (3)
[Chem. 6]

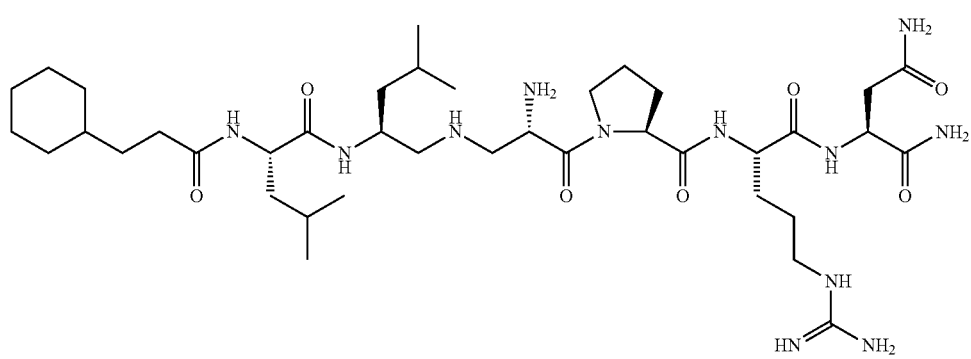

Formula (3)

CPN-220 was synthesized and purified in the same manner as Synthesis Example 1 by using 75 mg (0.044 mmol) of Rink Amide resin (0.58 mmol/g, WATANABE CHEMICAL INDUSTRIES, LTD.) (39.9 mg, yield 81%).
HRMS (ES+) calcd for (M⁺+H) 835.5512, found 835.5518.

Synthesis Example 34

Synthesis of Peptide Containing the Amino Acid Sequence of SEQ ID NO: 68 (Comparative Example): CPN-248

3-Cyclohexylpropionyl-Asp-Leu-Dbu-Pro-Arg-Asn-NH₂ (CPN-248)

CPN-248 was synthesized and purified in the same manner as Synthesis Example 1 by using 75 mg (0.044 mmol) of Rink Amide resin (0.58 mmol/g, WATANABE CHEMICAL INDUSTRIES, LTD.) (35.2 mg, yield 74%).
HRMS (ES+) calcd for (M⁺+H) 851.5103, found 851.5104.

Synthesis Example 35

Synthesis of Peptide Containing the Amino Acid Sequence of SEQ ID NO: 69 (Comparative Example): CPN-255

3-Cyclohexylpropionyl-Leu-Thr-Dbu-Pro-Arg-Asn-NH₂ (CPN-255)

CPN-255 was synthesized and purified in the same manner as Synthesis Example 1 by using 75 mg (0.044 mmol) of Rink Amide resin (0.58 mmol/g, WATANABE CHEMICAL INDUSTRIES, LTD.) (20.8 mg, yield 81%).
HRMS (ES+) calcd for (M⁺+H) 837.5310, found 837.5309.

Synthesis Example 36

Synthesis of Peptide Containing the Amino Acid Sequence of SEQ ID NO: 70 (Comparative Example): CPN-256

3-Cyclohexylpropionyl-Leu-Dbu-Dbu-Pro-Arg-Asn-NH₂ (CPN-256)

CPN-256 was synthesized and purified in the same manner as Synthesis Example 1 by using 75 mg (0.044 mmol) of Rink Amide resin (0.58 mmol/g, WATANABE CHEMICAL INDUSTRIES, LTD.) (37.8 mg, yield 66%).
HRMS (ES+) calcd for (M⁺+H) 836.5470, found 836.5470.

Synthesis Example 37

Synthesis of Peptide Containing the Amino Acid Sequence of SEQ ID NO: 71 (Comparative Example): CPN-257

3-Cyclohexylpropionyl-Leu-Asn-Dbu-Pro-Arg-Asn-NH₂ (CPN-257)

CPN-257 was synthesized and purified in the same manner as Synthesis Example 1 by using 75 mg (0.044 mmol) of Rink Amide resin (0.58 mmol/g, WATANABE CHEMICAL INDUSTRIES, LTD.) (29.8 mg, yield 63%).
HRMS (ES+) calcd for (M⁺+H) 850.5263, found 850.5262.

Synthesis Example 38

Synthesis of Peptide Containing the Amino Acid Sequence of SEQ ID NO: 72 (Comparative Example): CPN-258

3-Cyclohexylpropionyl-Leu-Asp-Dbu-Pro-Arg-Asn-NH$_2$ (CPN-258)

CPN-258 was synthesized and purified in the same manner as Synthesis Example 1 by using 75 mg (0.044 mmol) of Rink Amide resin (0.58 mmol/g, WATANABE CHEMICAL INDUSTRIES, LTD.) (35.2 mg, yield 74%).

HRMS (ES+) calcd for (M$^+$+H) 851.5103, found 851.5101.

Synthesis Example 39

Synthesis of Peptide Containing the Amino Acid Sequence of SEQ ID NO: 67 (Comparative Example): CPN-116

3-Cyclohexylpropionyl-Leu-Leu-Dpr-Pro-Arg-Asn-NH$_2$ (CPN-116)

The structure of CPN-116 is shown by the following formula (4).
[Chem. 7]

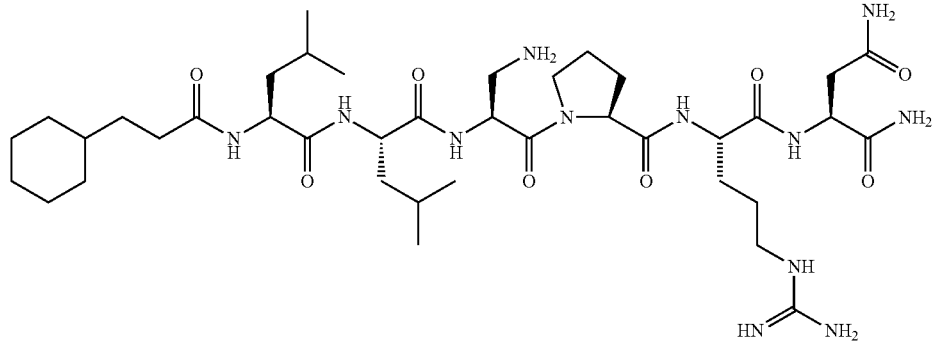

Formula (4)

CPN-116 was synthesized and purified in the same manner as Synthesis Example 33 except that Boc-Dpr(Fmoc)-OH is changed to Fmoc-Dpr(Boc)-OH (37.9 mg, yield 810).

<Evaluation of In Vitro Agonist Activity for Human Neuromedin U Receptor>

Test Example 1

For CPN-219 which has been synthesized in Synthesis Example 1, evaluation of the agonist activity for type 1 and type 2 human neuromedin U receptor (hNMUR1 and hNMUR2) was carried out according to the following method. The results are shown in FIG. 1. At a concentration of 100 nM, CPN-219 exhibited the NMUR2 selective agonist activity.

In FIG. 1, "hNMU" represents the result relating to human neuromedin U.

(1) Cell Culture

CHO cells derived from Chinese hamster ovary which stably express hNMUR1 or hNMUR2 were cultured in a 5% (v/v) CO$_2$ incubator at 37° C. by using MEM alpha (GIBCO (registered trademark), Thermo Fisher Scientific Inc.) medium containing 1 mg/mL G418 (NACALAI TESQUE, INC.), 10% (v/v) fetal bovine serum (FCS) and nucleosides (adenosine 10 mg/L, cytidine 10 mg/L, guanosine 10 mg/L, uridine 10 mg/L, 2'-deoxyadenosine 10 mg/L, 2'-deoxycytidine hydrochloride 11 mg/L, 2'-deoxyguanosine 10 mg/L, thymidine 10 mg/L).

(2) Evaluation of In Vitro Agonist Activity

The CHO cells were sown on a 96 well black-walled plate with clear bottom (Iwaki: AGC TECHNO GLASS CO., LTD.) at 2.0×10$^4$ cells per well (150 µL DMEM+10% (v/v) FBS), and then cultured for 18 hours.

After the culture, 100 µL of Fluo-4 AM (Promega Corporation) solution as a fluorescent indicator of intracellular calcium concentration was added to each well, in which the solution has been prepared such that it has the final concentration of 4 µM in assay buffer (HBSS, 10 mM HEPES, 2.5 mM probenecid, 1% (v/v) FCS: pH 7.4). After culture for 40 minutes at 37° C., the cells were washed 4 times with the assay buffer and set in a fluorometric imaging plate reader (Molecular Devices, LLC.).

The peptide as a test sample was dissolved by using dimethyl sulfoxide (DMSO) such that the stock solution is present at 20 mM, and then it was stored at 4° C. One hour before addition to the cells, by using an assay buffer added with 0.05% (v/v) bovine serum albumin (BSA) and 0001% (v/v) Triton (registered trademark) X-100, preparation to arbitrary final concentration was made (10$^{-12}$ to 10$^{-6}$ M), and the fluorescence based on the activity of recruiting intracellular calcium by the peptide (i.e., agonist activity) was measured by using a fluorometric imaging plate reader.

Test Example 2

For CPN-116 which has been synthesized in Synthesis Example 39, evaluation of the agonist activity for hNMUR1 and hNMUR2 was carried out according to the method of Test Example 1. The results are shown in FIG. 1.

Test Example 3

Figure 2:
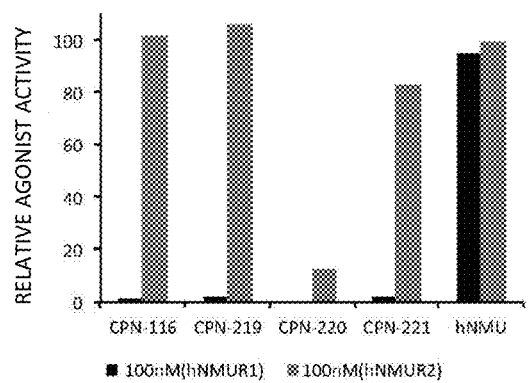
FIG. 2 illustrates the agonist activity for hNMUR1 and hNMUR2 by peptides of Examples and Comparative Examples.

For CPN-221 which has been synthesized in Synthesis Example 2 and CPN-220 which has been synthesized in Synthesis Example 33, evaluation of the agonist activity for hNMUR1 and hNMUR2 was carried out according to the test method of Test Example 1. The results are shown in FIG. 2. CPN-221 exhibited the hNMUR2 selective agonist activity at a concentration of 100 nM. On the other hand, CPN-220 did not exhibit the hNMUR2 selective agonist activity at a concentration of 100 nM.

In FIG. 2, "hNMU" represents the result relating to human neuromedin U.

Test Example 4

For the peptides which have been prepared in Synthesis Examples 3 to 32 and 34 to 38, evaluation of the agonist activity for hNMUR1 and hNMUR2 was carried out according to the test method of Test Example 1. The results are shown in FIGS. 3 to 5.

CPN-248 and CPN-255 to 258, which are Comparative Examples, did not exhibit the hNMUR2 selective agonist activity at a concentration of 100 nM.

On the other hand, CPN-219, CPN-227 to 247, and CPN-249 to 253, which are Examples, exhibited the hNMUR2 selective agonist activity at a concentration of 100 nM. In particular, CPN-219, CPN-227 to 247, and CPN-250 to 253 exhibited an excellent hNMUR2 selective agonist activity, and CPN-219, CPN-227 to 245, CPN-247, and CPN-250 to 253 exhibited even more excellent hNMUR2 selective agonist activity.

Figure 3:
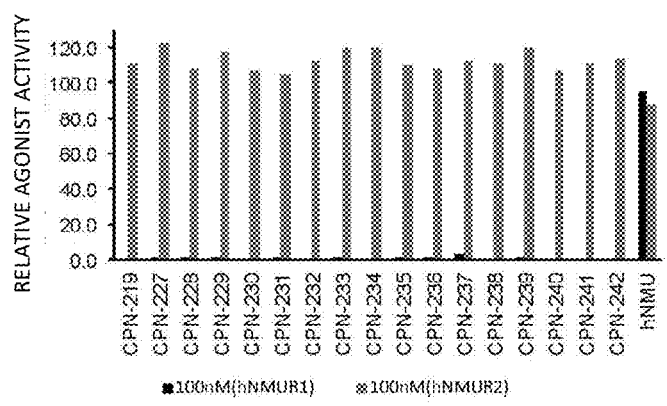
FIG. 3 illustrates the agonist activity for hNMUR1 and hNMUR2 by peptides of Examples.
Figure 4:
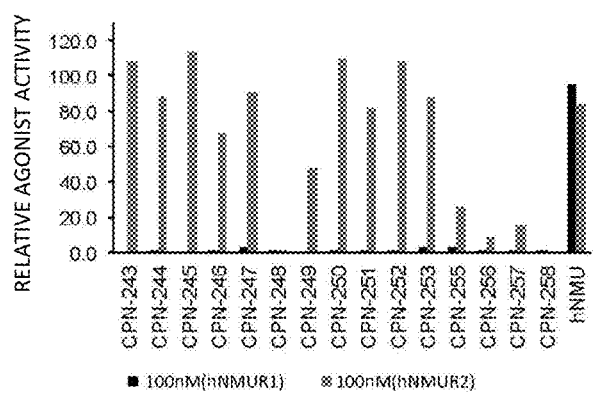
FIG. 4 illustrates the agonist activity for hNMUR1 and hNMUR2 by peptides of Examples and Comparative Examples.
Figure 5:
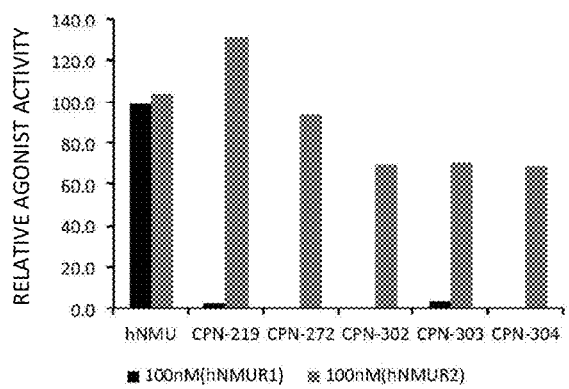
FIG. 5 illustrates the agonist activity for hNMUR1 and hNMUR2 by peptides of Examples.

In FIGS. 3 to 5, "hNMU" represents the result relating to human neuromedin U.

<Evaluation of In Vitro Agonist Activity for Mouse Neuromedin U Receptor>

Test Example 5

For CPN-219 which has been synthesized in Synthesis Example 1, evaluation of the agonist activity for type 1 and type 2 mouse neuromedin U receptor (mNMUR1 and mNMUR2) was carried out according to the following method.
(1) Cell Culture HEK293 cells derived from human embryonic kidney were cultured in a 5% (v/v) $CO_2$ incubator at 37° C. by using DMEM-high glucose (GIBCO (registered trademark), Thermo Fisher Scientific Inc.) medium containing 10% (v/v) FCS.
(2) Evaluation of In Vitro Agonist Activity Cells were sown on a 100 mm dish at $5.0 \times 10^5$ cells (10 mL DMEM+10% FBS), and then cultured for 18 hours. After the culture, by using FuGENE6 (Promega Corporation), the cultured cells were transfected with an expression plasmid which encodes mNMUR1 or mNMUR2 (2.5 μg). The cells were cultured for 18 hours. After that, the HEK293 cells were sown on a 96 well black-walled plate with clear bottom (Iwaki: AGC TECHNO GLASS CO., LTD.) at $3.0 \times 10^4$ cells per well (150 μL DMEM+10% (v/v) FBS), in which the plate has been previously coated with poly D-lysine, and then cultured for 18 hours.

On the next day, 100 μL of Fluo-4 AM (Promega Corporation) solution as a fluorescent indicator of intracellular calcium concentration was added to each well, in which the solution has been prepared such that it has the final concentration of 4 μM in assay buffer (HBSS, 10 mM HEPES, 2.5 mM probenecid, 1% FCS: pH 7.4). After culture for 40 minutes at 37° C., the cells were washed 4 times with the assay buffer and set in a fluorometric imaging plate reader (Molecular Devices, LLC.).

The peptide as a test sample was dissolved by using DMSO such that the stock solution is present at 20 mM, and then it was stored at 4° C. One hour before addition to the cells, by using an assay buffer added with 0.05% (v/v) BSA and 0.001% (v/v) Triton (registered trademark) X-100, preparation to arbitrary final concentration was made ($10^{-12}$ to $10^{-6}$ M), and the fluorescence based on the activity of recruiting intracellular calcium by the peptide (i.e., agonist activity) was measured by using a fluorometric imaging plate reader.

Figure 6:
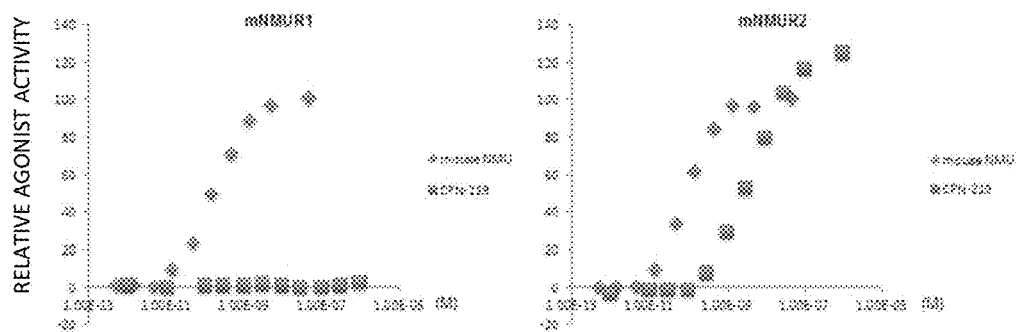
FIG. 6 illustrates the agonist activity for mNMUR1 and mNMUR2 by peptide of Examples.

The results are shown in FIG. 6. CPN-219 exhibited the mNMUR2 selective agonist activity at a concentration of 100 nM.

<Evaluation of Stability in Phosphate Buffer Solution>

Test Example 6

For CPN-219 which has been synthesized in Synthesis Example 1, evaluation was made according to the following method for determining the stability in a phosphate buffer solution.

Peptide solution was prepared (1 mL) by using a 100 mM phosphate buffer solution (pH 7.4) so as to have the final concentration of 1 mM, and then the peptide solution was incubated for arbitrary time period (1 to 72 hours) in a water bath at 37° C. After the arbitrary time period, sampling was carried out and 20 μL of injection into high performance liquid chromatography (HPLC) (column: COSMOSIL (registered trademark) Cholester Packed Column 4.6 mmI.D.× 150 mm; gradient: % B 25-35, 30 min [A: $H_2O$-0.1% (v/v) TFA; B: MeCN]; flow rate: 1.0 mL/min; measurement wavelength: 220 nm) was made. Then, by taking the obtained area value as an indicator, the stability was analyzed from the recovery rate (%) of the compound.

Figure 7:
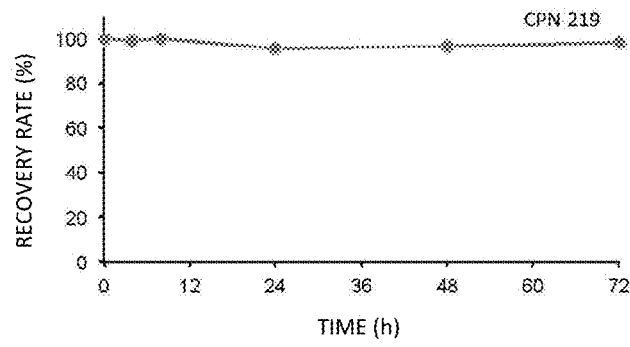
FIG. 7 illustrates the result of evaluating the stability of peptide of Example in a phosphate buffer solution.

The results are shown in FIG. 7. It was recognized that CPN-219 has recovery rate of 98% or higher in 100 mM phosphate buffer solution for 72 hours, and thus it can be stably present in a phosphate buffer solution.

Test Example 7

Figure 8:
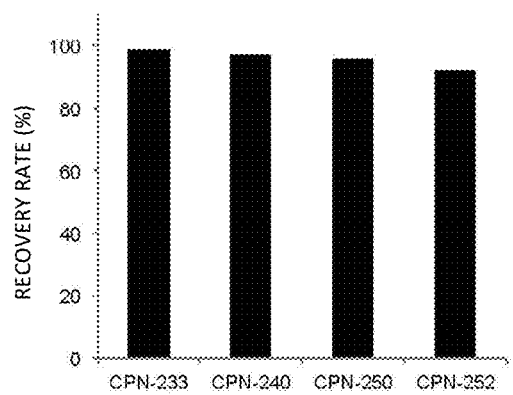
FIG. 8 illustrates the result of evaluating the stability of peptides of Example in a phosphate buffer solution.

Stability of CPN-233 which has been synthesized in Synthesis Example 9 in a phosphate buffer solution was evaluated by the same method as Test Example 6. The results are shown in FIG. 8. It was recognized that CPN-233 has recovery rate of 97% or higher in 100 mM phosphate buffer solution for 72 hours, and thus it can be stably present in a phosphate buffer solution.

Test Example 8

Stability of CPN-240 which has been synthesized in Synthesis Example 16 in a phosphate buffer solution was evaluated by the same method as Test Example 6. The results are shown in FIG. 8. It was recognized that CPN-240 has recovery rate of 97% or higher in 100 mM phosphate buffer solution for 72 hours, and thus it can be stably present in a phosphate buffer solution.

Test Example 9

Stability of CPN-250 which has been synthesized in Synthesis Example 25 in a phosphate buffer solution was evaluated by the same method as Test Example 6. The results are shown in FIG. 8. It was recognized that CPN-250 has recovery rate of 95% or higher in 100 mM phosphate buffer solution for 72 hours, and thus it can be stably present in a phosphate buffer solution.

Test Example 10

Stability of CPN-252 which has been synthesized in Synthesis Example 27 in a phosphate buffer solution was evaluated by the same method as Test Example 6. The results are shown in FIG. 8. It was recognized that CPN-252 has recovery rate of 92% or higher in 100 mM phosphate buffer solution for 72 hours, and thus it can be stably present in a phosphate buffer solution.

Test Example 11

Figure 9:
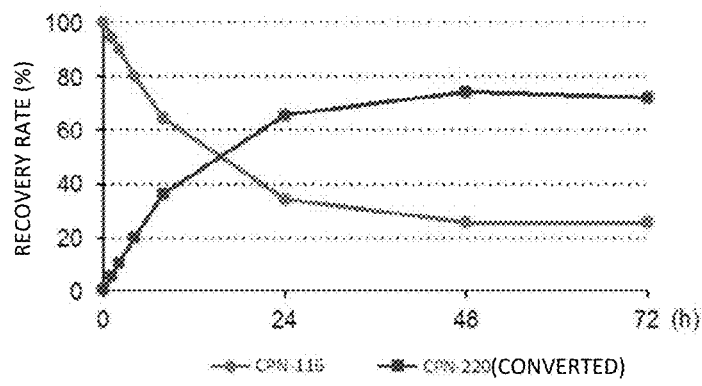
FIG. 9 illustrates the result of evaluating the stability of peptides of Comparative Examples in a phosphate buffer solution.

Stability of CPN-116 (Comparative Example) which has been synthesized in Synthesis Example 39 in a phosphate buffer solution was evaluated by the same method as Test Example 6. The results are shown in FIG. 9. After 48 hours, 70% or more of CPN-116 was converted to CPN-220 in 100 mM phosphate buffer solution.

Test Example 12

Figure 10:
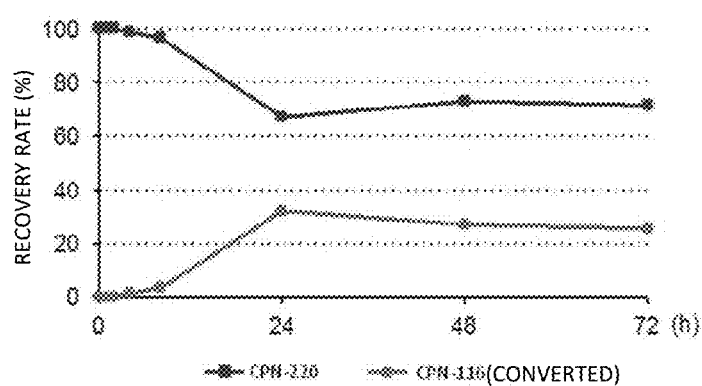
FIG. 10 illustrates the result of evaluating the stability of peptides of Comparative Examples in a phosphate buffer solution.

Stability of CPN-220 (Comparative Example) which has been synthesized in Synthesis Example 33 in a phosphate buffer solution was evaluated by the same method as Test Example 6. The results are shown in FIG. 10. After 48 hours, 25% or more of CPN-220 was converted to CPN-116 in 100 mM phosphate buffer solution.

It was recognized from Test Examples 11 and 12 that, since 70% or more of CPN-116 was converted to CPN-220 that does not show the hNMUR2 selective agonist activity, CPN-116 is chemically unstable.

<Evaluation of Stability in Rat Plasma>

Test Example 13

To determine the stability of CPN-219 synthesized in Synthesis Example 1 in rat plasma, the evaluation was made according to the following method.

Peptide solution was added to rat plasma such that the final peptide concentration is 50 µg/mL, and then incubated for arbitrary time period (0.5 to 6 hours) at 37° C. After the arbitrary time period, sampling was carried out and high performance liquid chromatography mass spectrometry (LC/MS) was performed under the following conditions followed by stability analysis.

LC/MS System: LC-MS2020 (SHIMADZU CORPORATION)

Column: TSKgel ODS-100V (Tosoh Corporation, 3.0 µm, 2.0 mm×75 mm)

Mobile layer: 0.1% trifluoroacetic acid (pH 2.5):acetonitrile=2:1

Flow rate: 0.2 mL/min

Column temperature: 40° C.

Detection: ESI$^+$, m/z=425.

Figure 11:
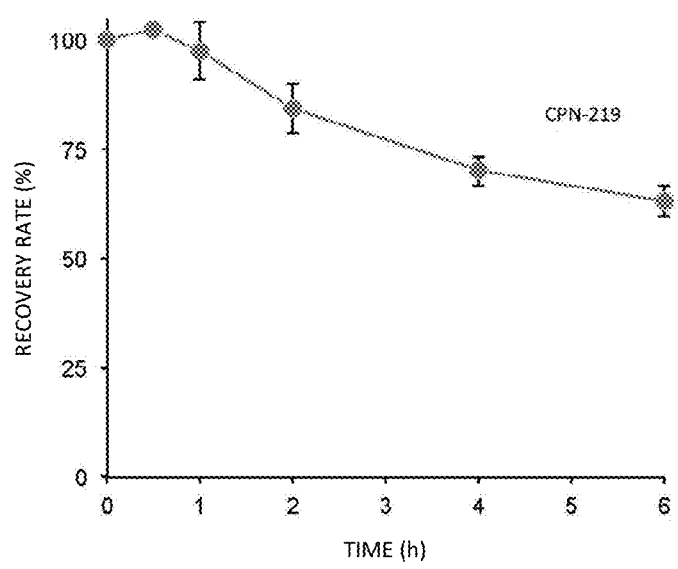
FIG. 11 illustrates the result of evaluating the stability of peptide of Example in rat plasma.

The results are shown in FIG. 11. It was found that CPN-219 has recovery rate of 80% or higher after 2 hours, or 60% or higher after 6 hours in rat plasma, and thus it can stably be present in rat plasma.

Test Example 14

For CPN-116 (Comparative Example) which has been synthesized in Synthesis Example 39, stability in rat plasma was evaluated according to the method of Test Example 48.

Figure 12:
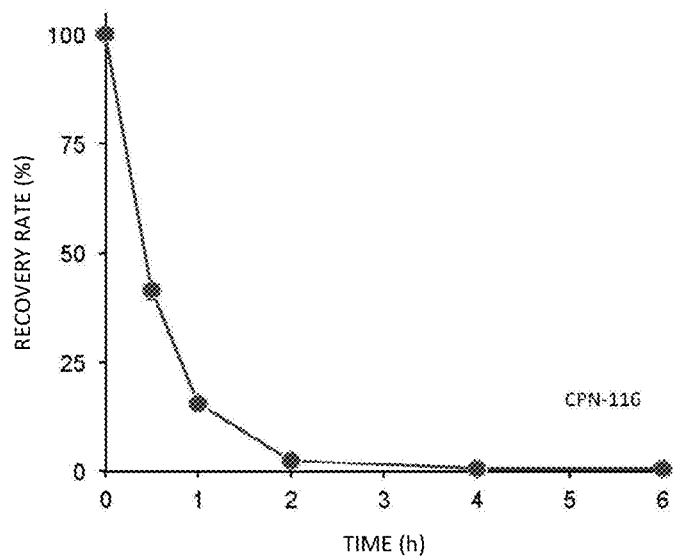
FIG. 12 illustrates the result of evaluating the stability of peptide of Comparative Example in rat plasma.

The results are shown in FIG. 12. It was found that, after 2 hours, the recovery rate from rat plasma was 3% or lower for CPN-116.

<Evaluation of Pharmacokinetics of Peptides in Rat>

Test Example 15

For CPN-219 which has been synthesized in Synthesis Example 1 and CPN-116 (Comparative Example) which has been synthesized in Synthesis Example 39, pharmacokinetics of peptides in rats was evaluated according to the following method.

The peptide solution (500 µg/200 µL) was administered via jugular vein of a Wistar rat. After arbitrary time period (1 to 240 minutes), blood was taken from the femoral artery which has been subjected to cannulation in advance. According to the LC/MS analysis, pharmacokinetics of the peptide was analyzed. The LC/MS analysis was carried out under the same conditions as above.

Figure 13:
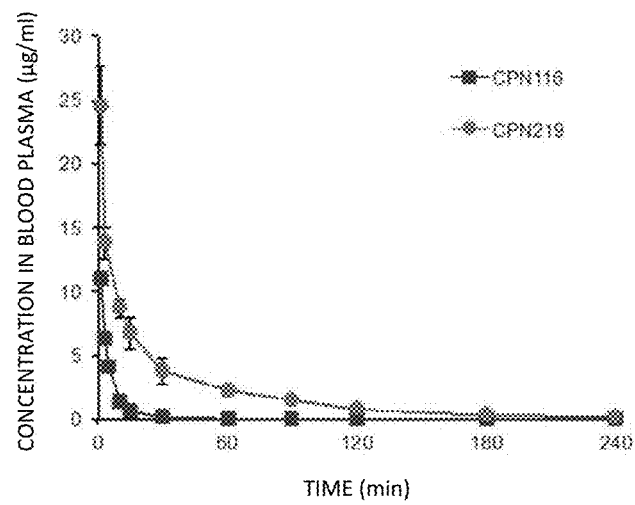
FIG. 13 illustrates the result of evaluating the pharmacokinetics of peptides in rats of Example and Comparative Example.

The results are shown in FIG. 13. Compared to CPN-116, CPN-219 shows more favorable pharmacokinetics in rat blood.

<Evaluation of Activity of Suppressing Body Weight Gain According to Administration into Body of Mouse>

Test Example 16

In order to determine the effect of suppressing body weight gain according to administration of CPN-219, which has been synthesized in Synthesis Example 1, into body of a mouse, the evaluation was carried out according to the following method.

CPN-219, each dissolved at 64 µg or 213 µg in physiological saline (5 µL), was administered once to the nasal cavity of a ddy male mouse under anesthetization. As a control, physiological saline (5 µL) was administered once to the nasal cavity. For each administration group, the body weight of a mouse and food intake amount were measured immediately before the administration, each of Day 1 to 5 from immediately after the administration.

The body weight of a mouse was 29.0±0.83 g for the group with intranasal administration of 64 µg, or 27.7±1.29 g for the group with intranasal administration of 213 µg.

Figure 14:
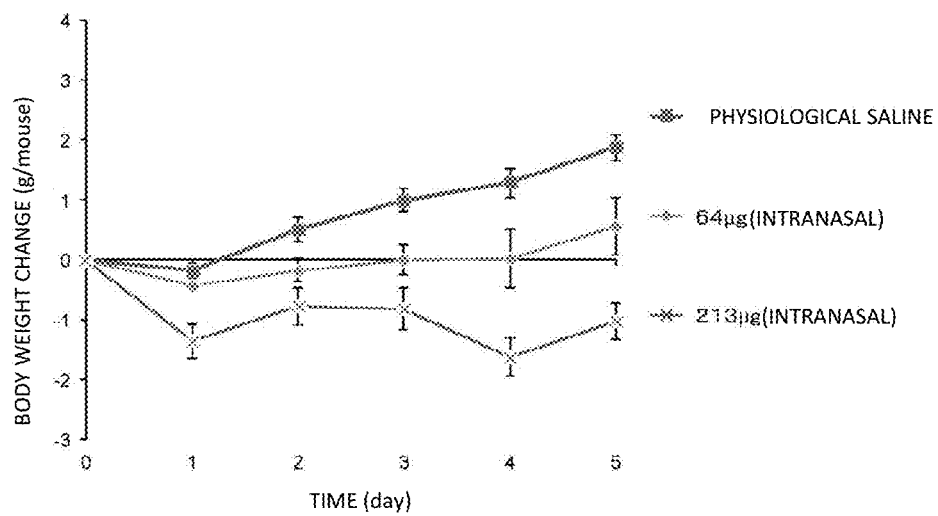
FIG. 14 illustrates the result of evaluating the activity of suppressing body weight gain by peptide of Example upon intranasal administration to a mouse.
Figure 15:
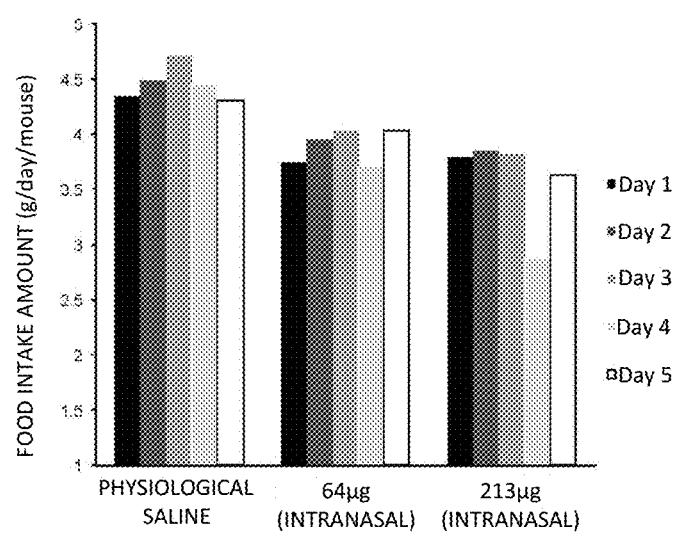
FIG. 15 illustrates the result of evaluating the food intake amount of peptide of Example upon intranasal administration to a mouse.

The results are shown in FIG. 14 and FIG. 15. Upon the administration to a body, CPN-219 significantly suppressed the body weight gain of a mouse and food intake.

<Evaluation of Brain Delivery>

Test Example 17

For CPN-219 which has been synthesized in Synthesis Example 1 and CPN-116 (Comparative Example) which has been synthesized in Synthesis Example 39, the brain delivery upon intranasal administration to a mouse was evaluated according to the following method.

Peptide solution (200 µg/5 µL) was administered to the nasal cavity of a ddY male mouse. After 5 minutes, the animal was sacrificed and the brain tissues were collected. According to the LC/MS analysis, concentration of the peptide in plasma and brain was analyzed, and the ratio of concentration in brain compared to concentration in plasma was analyzed. The LC/MS analysis was carried out under the same conditions as above.

Figure 16:
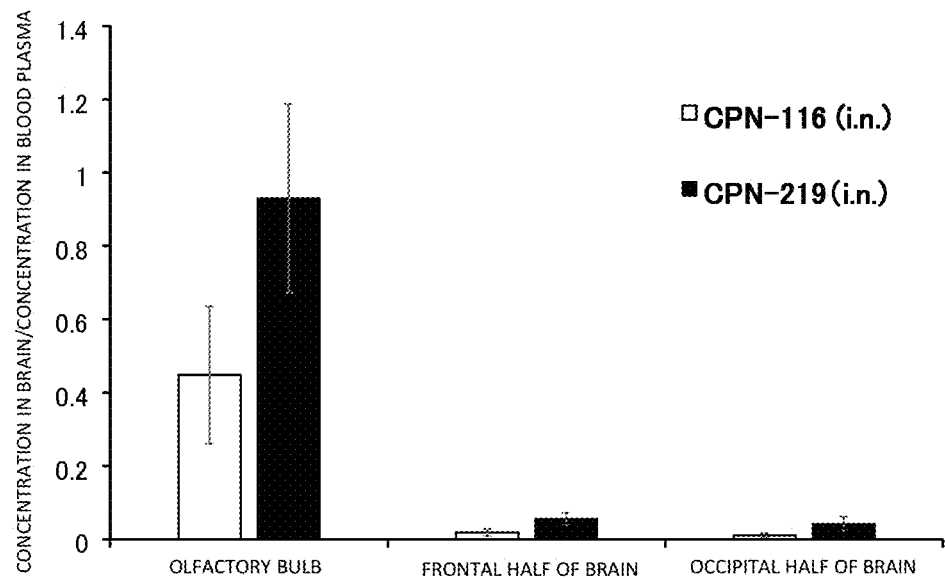
FIG. 16 illustrates the result of evaluating the brain delivery of peptides of Example and Comparative Example.

The results are shown in FIG. 16. Upon the intranasal administration to a mouse, CPN-219 exhibited more favorable transfer to an olfactory bulb compared to CPN-116.

<Evaluation of Fluctuation in Corticosterone Concentration in Blood>

Test Example 18

With regard to CPN-219 which has been synthesized in Synthesis Example 1, in order to determine the influence of intranasal administration (i.n.) to a mouse on corticosterone concentration in blood, the evaluation was carried out according to the following method. As a control test, intraperitoneal administration (i.p.) of CPN-219 to a mouse was carried out.

Peptide solution (200 μg/5 μL) or physiological saline (5 μL) was administered, either intranasally or peritoneally, to a ddY male mouse. After 5 minutes, blood was taken from the caval vein, and corticosterone concentration in plasma was analyzed according to the LC/MS analysis. Furthermore, as a control, without administering the peptide solution (200 μg/5 μL) or physiological saline (5 μL), blood was taken after minutes from the caval vein, and corticosterone concentration in plasma was analyzed according to the LC/MS analysis. The LC/MS analysis was carried out under the same conditions as above.

Figure 17:
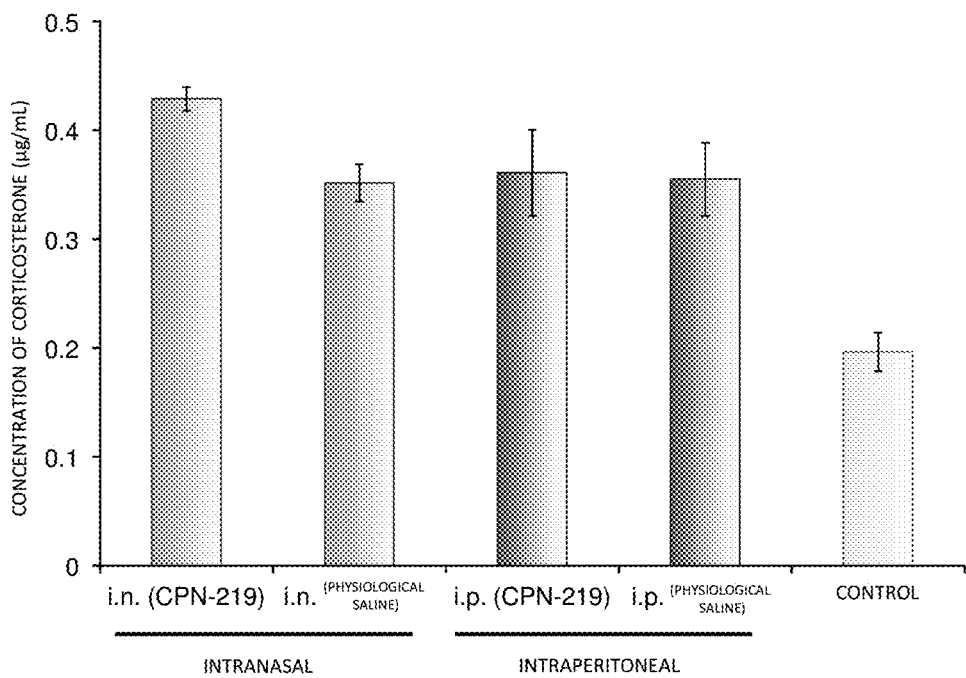
FIG. 17 illustrates the result of evaluating the fluctuation in blood corticosterone by peptide of Example.

The results are shown in FIG. 17. It was recognized that, upon the intranasal administration, CPN-219 significantly increased the corticosterone concentration in blood. This result indicates a possibility that CPN-219 activates the NMUR2 receptor in brain and exhibits the function via CRH.

<Evaluation of Activity of Suppressing Increase in Prolactin Concentration in Blood>

Test Example 19

With regard to CPN-219 which has been synthesized in Synthesis Example 1, in order to determine the influence of intranasal administration (i.n.) to a mouse on prolactin (PLT) concentration in blood, the evaluation was carried out according to the following method. As a control test, administration of physiological saline was carried out.

Peptide solution (200 μg/5 μL) or physiological saline (5 μL) was administered to the nasal cavity of a ddY male mouse. After 20 minutes, restraint stress (i.e., addition to the inside of a tube) was applied for 20 minutes and blood was taken by cutting off the animal head. Then, the PLT concentration in plasma was analyzed by using Mouse Prolactin DuoSet ELISA (R&D systems).

Furthermore, for a ddY male mouse which has not been administered with the peptide solution (200 μg/5 μL) or physiological saline (5 μL), and also not applied with any stress, the PLT concentration in plasma was analyzed in the same manner as above.

Figure 18:
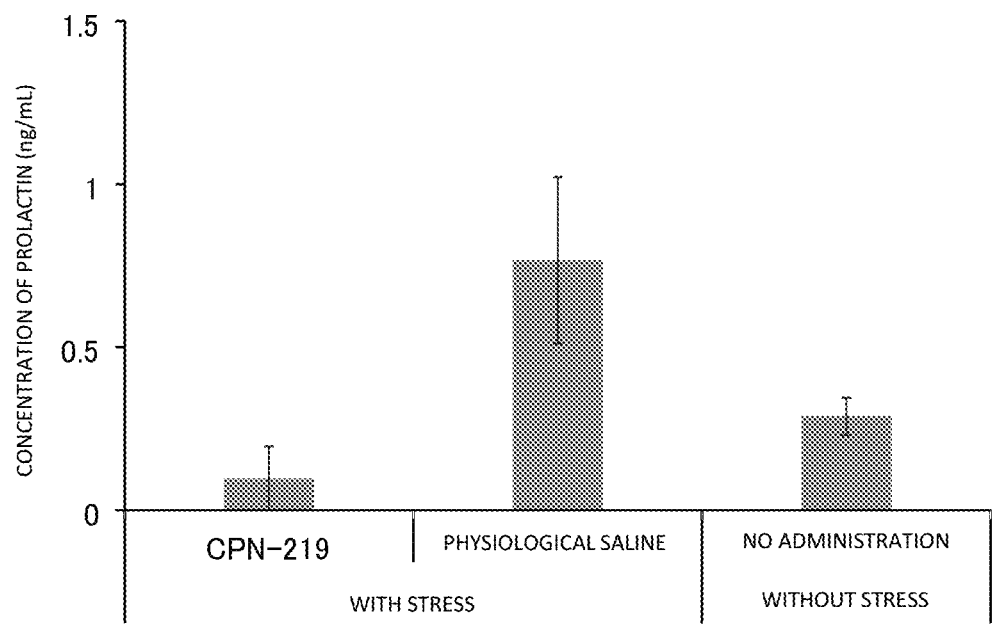
FIG. 18 illustrates the result of evaluating the activity of suppressing an increase in blood prolactin concentration by peptide of Example.

The results are shown in FIG. 18. It was recognized that CPN-219 suppresses the prolactin secretion following the intranasal administration.

The present application is based on Japanese Patent Application No. 2017-008301, which has been filed on Jan. 20, 2017, and the disclosure thereof is entirely cited by reference.

The invention claimed is:

1. A peptide represented by a following Formula (1) or a pharmaceutically acceptable salt thereof:

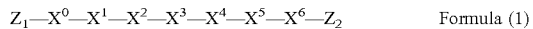
$$Z_1-X^0-X^1-X^2-X^3-X^4-X^5-X^6-Z_2 \quad \text{Formula (1)}$$

in the above Formula (1), $X^0$ is a 3-cyclohexylalanine residue or absent;

$X^1$ is an amino acid residue selected from the group consisting of Leu, Val, Ile, Thr, Asn, Gln, norvaline, isovaline, norleucine, 2-cyclohexylglycine, 3-cyclohexylalanine, 2,4-diaminobutanoic acid, and 2-aminobutyric acid;

$X^2$ is an amino acid residue selected from the group consisting of Leu, Val, Ile, norvaline, isovaline, norleucine, and 2-cyclohexylglycine;

$X^3$ is a residue of 2,4-diaminobutanoic acid;

$X^4$ is a Pro residue or a homoproline residue;

$X^5$ is an Arg residue;

$X^6$ is an Asn residue;

$Z_1$ is a hydrogen atom or $R_1-(R_2)n-CO-$; $R_1$ is a hydrogen atom or a hydroxy group, or a substituted or unsubstituted chain hydrocarbon group, alicyclic hydrocarbon group, aromatic hydrocarbon group, or heterocyclic group; $R_2$ is an alkylene group, an oxyalkylene group, or an alkyleneoxy group; and n is 0 or 1; and $Z_2$ is an amino group, a hydrogen atom, a hydroxy group, an alkoxy group, a hydrocarbon group, or a polyalkylene glycol group, provided that the peptide represented by formula (I) does not comprise the amino acid sequence that is represented by SEQ ID NO: 17.

2. The peptide or the pharmaceutically acceptable salt thereof according to claim 1, wherein the $X^0$ is absent.

3. The peptide or the pharmaceutically acceptable salt thereof according to claim 1, wherein in the $Z_1$, $R_1$ is a substituted or unsubstituted alicyclic group having 3 to 12 carbon atoms or aromatic hydrocarbon group having 6 to 20 carbon atoms; $R_2$ is an alkylene group having 1 to 3 carbon atoms, an oxyalkylene group having 1 to 3 carbon atoms, or an alkyleneoxy group having 1 to 3 carbon atoms; and n is 1.

4. The peptide or the pharmaceutically acceptable salt thereof according to claim 1, wherein the $X^2$ is an amino acid residue selected from the group consisting of Leu, Ile, norvaline, norleucine, and 2-cyclohexylglycine.

5. The peptide or the pharmaceutically acceptable salt thereof according to claim 1, wherein the $X^1$ is an amino acid residue selected from the group consisting of Leu, Val, Ile, Thr, Asn, norvaline, norleucine, 2-cyclohexylglycine, and 3-cyclohexylalanine.

6. The peptide or the pharmaceutically acceptable salt thereof according to claim 1, wherein the peptide represented by Formula (1) comprises any one of the amino acid sequences that are represented by SEQ ID NOs: 1, 3 to 16, 18 and 36 to 50.

7. The peptide or the pharmaceutically acceptable salt thereof according to claim 6, wherein the peptide represented by Formula (1) comprises any one of the amino acid sequences that are represented by SEQ ID NOs: 1, 3 to 16 and 18.

8. A pharmaceutical composition comprising the peptide or the pharmaceutically acceptable salt thereof according to claim 1.

9. A method for treatment of metabolic syndrome, obesity, or diabetes comprising administering an effective amount of the peptide or the pharmaceutically acceptable salt thereof according to claim 1 to a patient.

10. A method for treatment of prolactin secretion-related disorder comprising administering an effective amount of the peptide or the pharmaceutically acceptable salt thereof according to claim 1 to a patient.

11. The method for treatment according to claim 10, wherein the prolactin secretion-related disorder is selected from the group consisting of Parkinson syndrome, acromegaly, hypophyseal gigantism, pituitary adenoma with high prolactin in blood, prolactinoma, diencephalon tumor, ovulation disorder with high prolactin in blood, puerperal galactischia, galactorrhea, amenorrhea syndrome with galactorrhea, sterility, menstrual disorder, peripartum cardiomyopathy, restless leg syndrome, autoimmune disease, impotence, Chiari-Frommel syndrome, Argonz-del Castillo syndrome, Forbes-Albright syndrome, lymphoma, Sheehan's syndrome, and spermatogenesis disorder.

* * * * *